US012661008B2

(12) United States Patent
Burwinkel

(10) Patent No.: US 12,661,008 B2
(45) Date of Patent: Jun. 23, 2026

(54) EAR-WORN DEVICES FOR TRACKING EXPOSURE TO HEARING DEGRADING CONDITIONS

(71) Applicant: Starkey Laboratories, Inc., Eden Prairie, MN (US)

(72) Inventor: Justin R. Burwinkel, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 827 days.

(21) Appl. No.: 17/641,742

(22) PCT Filed: Sep. 3, 2020

(86) PCT No.: PCT/US2020/049202
§ 371 (c)(1),
(2) Date: Mar. 9, 2022

(87) PCT Pub. No.: WO2021/050354
PCT Pub. Date: Mar. 18, 2021

(65) Prior Publication Data
US 2022/0313089 A1 Oct. 6, 2022

Related U.S. Application Data

(60) Provisional application No. 62/899,404, filed on Sep. 12, 2019.

(51) Int. Cl.
H04R 29/00 (2006.01)
A61B 5/00 (2006.01)

(52) U.S. Cl.
CPC ......... A61B 5/0022 (2013.01); H04R 29/008 (2013.01); H04R 2225/41 (2013.01); H04R 2225/61 (2013.01)

(58) Field of Classification Search
CPC ..... A61B 5/0022; H04R 29/008; H04R 29/00
See application file for complete search history.

(56) References Cited

U.S. PATENT DOCUMENTS 3,802,535 A * 4/1974 Peake ...................... G01H 3/00
                                                    73/647
4,307,385 A * 12/1981 Evans ...................... G01H 3/14
                                                    73/647

(Continued)

FOREIGN PATENT DOCUMENTS

RU        2281509      8/2006
RU        2660533      7/2018

(Continued)

OTHER PUBLICATIONS

"Comments & Recommendations on Noise & Hearing Conservation Regulations," Presented to The Honorable Joseph Dear, Assistant Secretary of Labor for Occupational Safety & Health by The National Hearing Conservation Association and the American Speech-Language-Hearing Association, May 26, 1994 (28 pages).

(Continued)

*Primary Examiner* — Olisa Anwah
(74) *Attorney, Agent, or Firm* — Pauly, DeVries Smith & Deffner LLC

(57) ABSTRACT

Embodiments herein relate to ear-worn devices that can track exposure to hearing degrading conditions and/or provide notifications or warnings regarding the same. In an embodiment, an ear-worn device is included having a control circuit, a microphone in electrical communication with the control circuit, an electroacoustic transducer for generating sound in electrical communication with the control circuit, and a power supply circuit in electrical communication with the control circuit, wherein the ear-worn device is configured to track exposure to hearing degrading conditions over time via at least one of the microphone and a (Continued)

sensor package and wherein the ear-worn device is configured to store data regarding the tracked exposure. Other embodiments are also included herein.

19 Claims, 8 Drawing Sheets

(56)                    References Cited

U.S. PATENT DOCUMENTS

| | | | | |
|---|---|---|---|---|
| 5,699,809 | A | 12/1997 | Combs et al. | |
| 5,878,782 | A | 3/1999 | Nakajima | |
| 6,456,199 | B1 * | 9/2002 | Michael | G01H 3/14 |
| | | | | 340/573.1 |
| 7,133,715 | B1 | 11/2006 | Smits et al. | |
| 7,151,835 | B2 * | 12/2006 | Yonovitz | G01H 3/14 |
| | | | | 381/72 |
| 7,401,519 | B2 * | 7/2008 | Kardous | G01H 3/14 |
| | | | | 381/72 |
| 7,786,100 | B2 | 8/2010 | Miller et al. | |
| 7,951,845 | B2 | 5/2011 | Miller et al. | |
| 8,923,543 | B2 | 12/2014 | Sacha et al. | |
| 9,167,356 | B2 | 10/2015 | Higgins et al. | |
| 9,381,119 | B2 * | 7/2016 | Michael | G01H 3/14 |
| 9,848,273 | B1 | 12/2017 | Helwani et al. | |
| 10,068,451 | B1 * | 9/2018 | Werner | H04R 29/00 |
| 11,944,517 | B2 * | 4/2024 | Kvaløy | H04R 1/1083 |
| 2006/0013858 | A1 | 1/2006 | Trune | |
| 2009/0075306 | A1 | 3/2009 | Tuohy et al. | |
| 2010/0278350 | A1 * | 11/2010 | Rung | H04R 1/10 |
| | | | | 381/59 |
| 2012/0076313 | A1 | 3/2012 | Junius et al. | |
| 2013/0090938 | A1 * | 4/2013 | Fishman | G16H 40/67 |
| | | | | 705/2 |
| 2013/0094658 | A1 * | 4/2013 | Holter | G10K 11/17861 |
| | | | | 381/72 |
| 2013/0095071 | A1 | 4/2013 | Bance et al. | |
| 2013/0095701 | A1 | 4/2013 | Golko et al. | |
| 2014/0247948 | A1 | 9/2014 | Goldstein | |
| 2015/0227708 | A1 * | 8/2015 | Jung | G16H 20/10 |
| | | | | 705/2 |
| 2015/0382120 | A1 | 12/2015 | Baskaran et al. | |
| 2016/0324478 | A1 | 11/2016 | Goldstein | |
| 2017/0300631 | A1 * | 10/2017 | Bertrand | G16H 10/60 |
| 2017/0374444 | A1 | 12/2017 | McNeill et al. | |
| 2017/0374478 | A1 * | 12/2017 | Jones | G10L 21/0364 |
| 2018/0046772 | A1 * | 2/2018 | Mitteldorf | A61B 5/0022 |
| 2018/0317837 | A1 | 11/2018 | Burwinkel et al. | |
| 2020/0245938 | A1 | 8/2020 | Xu et al. | |
| 2020/0382868 | A1 * | 12/2020 | Felton | G06F 3/0482 |
| 2021/0236339 | A1 * | 8/2021 | Bonnet | A61B 5/6817 |

FOREIGN PATENT DOCUMENTS

| | | |
|---|---|---|
| WO | 2020236911 | 11/2020 |
| WO | 2021050354 | 3/2021 |

OTHER PUBLICATIONS

"Diabetes and Hearing Loss," American Diabetes Association resource available at least as early as Mar. 24, 2022 at URL <https://www.diabetes.org/diabetes/diabetes-and-hearing-loss> (4 pages).
"Enlarged Vestibular Aqueducts and Childhood Hearing Loss," US Department of Health and Human Services, National Institute of Health, 2012 NIDCD Fact Sheet, Hearing and Balance (4 pages).

"International Preliminary Report on Patentability," for PCT Application No. PCT/US2020/049202 mailed Mar. 24, 2022 (11 pages).
"International Search Report and Written Opinion," for PCT Application No. PCT/US2020/049202 mailed Nov. 4, 2020 (16 pages).
"What Is Type 2 Diabetes? Symptoms, Causes, Diagnosis, Treatment, and Prevention," Everyday Health Guide available at least as early as Apr. 14, 2016 at URL <https://www.everydayhealth.com/type-2-diabetes/guide/> (41 pages).
Bauman, Neil "Strenuous Exercise and Resulting Hearing Loss," Center for Hearing Loss Help blog post. Apr. 10, 2016. Accessible at URL <hearinglosshelp.com/blog/strenuous-exercise-and-resulting-hearing-loss/> (6 pages).
Campbell, Kathleen C.M., et al. "Drug-Induced Ototoxicity: Diagnosis and Monitoring," Drug Safety, May 2018, vol. 41(5), pp. 451-464 (14 pages).
Fan, Dongyan, et al. "Influence of high-altitude hypoxic environments on the survival of cochlear hair cells and spiral ganglion neurons in rats," Biomedical Reports 5: 681-685, 2016 (5 pages).
Fechter, Laurence D., et al. "Predicting Exposure Conditions that Facilitate the Potentiation of Noise-Induced Hearing Loss by Carbon Monoxide," Toxicological Sciences, 58, 315-323 (2000), 9 pages.
Hayes, Kristin "The Relationship Between Hearing Loss and Exercise," Verywellhealth article available at least as early as Aug. 16, 2020 at URL <https://www.verywellhealth.com/how-does-exercise-affect-hearing-loss-4129369> (6 pages).
Johnson, Patricia T. "Noise Exposure: Explanation of OSHA and NIOSH Safe-Exposure Limits and the Importance of Noise Dosimetry," Etymotic Research Inc., 2014 (8 pages).
Nakashima, Tsutomu, et al. "Air-Bone Gap and Resonant Frequency in Large Vestibular Aqueduct Syndrome," The American Journal of Otology, vol. 21, No. 5, 2000 pp. 671-674 (4 pages).
Nassrallah, Flora, et al. "An indirect calculation method for estimating occupational sound exposure from communication headsets," The Journal of the Acoustical Society of America 145, 749 (2019) (12 pages).
Neitzel, Richard, et al. "Determination of Risk of Noise-Induced Hearing Loss due to Recreational Sound: Review," World Health Organization, WHO Make Listening Safe: Risk Assessment and Definitions group publication, Feb. 2017 (25 pages).
Nies, Eberhard "Ototoxic Substances at the Workplace: A Brief Update*," Arh Hig Rada Toksikol 2012;63: 147-152 (6 pages).
Noordman, Bo Jan, et al. "Prognostic Factors for Sudden Drops in Hearing Level After Minor Head Injury in Patients with an Enlarged Vestibular Aqueduct: A Meta-analysis," Otology & Neurology 36:4-11 (2014) (8 pages).
Nuttall, Alfred "Sound-induced cochlear ischemia/hypoxia as a mechanism of hearing loss," Noise & Health 1999, vol. 2, Iss. 5, pp. 17-31 (10 pages).
Rabinowitz, Peter M. "Noise-induced hearing loss," American Family Physician; Leawood vol. 61, Iss. 8, May 1, 2000 pp. 2749-2756, 2759-60 (11 pages).
Smith, Bridget A., et al. "Audiovestibular findings in children with enlarged vestibular aqueduct," ENT and Audiology News, Nov./Dec. 2015, vol. 24, No. 5 (4 pages).
Yan, Lu, et al. "Saturated hydrogen saline protects against noise-induced hearing loss," Journal of Otology 2011, vol. 6, No. 1, pp. 36040 (5 pages).
Zhou, Guangwei, et al. "Characteristics of Vestibular Evoked Myogenic Potentials in Children with Enlarged Vestibular Aqueduct," The Laryngoscope 121: Jan. 2011, 220-226 (6 pages).
"Communication pursuant to Article 94(3) EPC," for European Patent Application No. 20772514.4 (our file 371.0022EPWO) mailed Jul. 9, 2025 (5 pages).

* cited by examiner

EAR-WORN DEVICES FOR TRACKING EXPOSURE TO HEARING DEGRADING CONDITIONS

This application is being filed as a PCT International Patent application on Sep. 3, 2020, in the name of Starkey Laboratories, Inc., a U.S. national corporation, applicant for the designation of all countries, and Justin R. Burwinkel, a U.S. Citizen, inventor(s) for the designation of all countries, and claims priority to U.S. Provisional Patent Application No. 62/899,404, filed Sep. 12, 2019, the contents of which are herein incorporated by reference in its entirety.

FIELD

Embodiments herein relate to ear-worn devices. More specifically, embodiments herein relate to ear-worn devices that can track exposure to hearing degrading conditions and/or provide notifications or warnings regarding the same.

BACKGROUND

Exposure to various conditions can degrade hearing over time. For example, exposure to sufficient levels of noise for sufficient amounts of time can result in noise-induced hearing degradation over time. Generally, the louder the noise, the less time of exposure is regarded in order to result in hearing damage.

Some people may also have conditions that put them at greater risk of hearing damage under certain circumstances. By way of example, enlarged vestibular aqueduct (EVA) describes a condition involving an abnormality of the vestibular aqueduct wherein exposure to sudden, jarring head movement can result in permanent hearing damage.

SUMMARY

Embodiments herein relate to ear-worn devices that can track exposure to hearing degrading conditions and/or provide notifications or warnings regarding the same. In a first aspect, an ear-worn device is included having a control circuit, a microphone in electrical communication with the control circuit, an electroacoustic transducer for generating sound in electrical communication with the control circuit, and a power supply circuit in electrical communication with the control circuit, wherein the ear-worn device is configured to track exposure to hearing degrading conditions over time via at least one of the microphone and a sensor package and wherein the ear-worn device is configured to store data regarding the tracked exposure.

In a second aspect, in addition to one or more of the preceding or following aspects, or in the alternative to some aspects, the sensor package can include at least one of a motion sensor, an oximeter, a glucometer, an air pressure sensor, a heart rate sensor, a blood pressure sensor, and an ambient air chemical sensor.

In a third aspect, in addition to one or more of the preceding or following aspects, or in the alternative to some aspects, the stored data regarding tracked exposure can include sound volume or vibration exposure, duration of exposure, and at least one of concurrent movement, concurrent position, concurrent oxygen saturation, concurrent blood glucose concentrations, concurrent heart rate, concurrent blood pressure, and concurrent ambient air chemical sensor data.

In a fourth aspect, in addition to one or more of the preceding or following aspects, or in the alternative to some aspects, stored data regarding tracked exposure can include sound volume or vibration exposure, duration of exposure, and a risk index factor calculated using at least one of concurrent movement, concurrent position, concurrent oxygen saturation, concurrent blood glucose concentrations, concurrent heart rate, concurrent blood pressure, concurrent ambient air chemical sensor data, and sound or vibration exposure during a preceding time period.

In a fifth aspect, in addition to one or more of the preceding or following aspects, or in the alternative to some aspects, the ear-worn device or an accessory device in communication therewith can further be configured to issue a warning if the tracked exposure crosses a dynamic threshold based upon a time period's combined exposure intensity and duration.

In a sixth aspect, in addition to one or more of the preceding or following aspects, or in the alternative to some aspects, the ear-worn device or an accessory device in communication therewith can be further configured to issue a warning if the tracked exposure crosses an instantaneous threshold value or a defined time total of exposure threshold value.

In a seventh aspect, in addition to one or more of the preceding or following aspects, or in the alternative to some aspects, the warning can be provided as at least one of an audible warning, a visual warning, and a haptic warning.

In an eighth aspect, in addition to one or more of the preceding or following aspects, or in the alternative to some aspects, the warning can be provided to at least one of the ear-worn device wearer and a third party.

In a ninth aspect, in addition to one or more of the preceding or following aspects, or in the alternative to some aspects, the ear-worn device or an accessory device in communication therewith can be further configured to issue preventative instructions to the ear-worn device wearer if the tracked exposure crosses an instantaneous threshold value or a defined time total exposure threshold value.

In a tenth aspect, in addition to one or more of the preceding or following aspects, or in the alternative to some aspects, the preventative instructions can be provided as at least one of an audible warning, a visual warning, and a haptic warning.

In an eleventh aspect, in addition to one or more of the preceding or following aspects, or in the alternative to some aspects, the ear-worn device or an accessory device in communication therewith can be configured to predict when an ear-worn device wearer will cross a threshold value.

In a twelfth aspect, in addition to one or more of the preceding or following aspects, or in the alternative to some aspects, the ear-worn device or an accessory device in communication therewith can be configured to predict when an ear-worn device wearer will cross a threshold value based on prior exposure data.

In a thirteenth aspect, in addition to one or more of the preceding or following aspects, or in the alternative to some aspects, the ear-worn device or an accessory device in communication therewith can be configured to send a prediction of when an ear-worn device wearer will cross a threshold value to an employer.

In a fourteenth aspect, in addition to one or more of the preceding or following aspects, or in the alternative to some aspects, the ear-worn device or an accessory device in communication therewith can be further configured to initiate a protective countermeasure if the tracked exposure crosses an instantaneous threshold value or a defined time total of exposure threshold value.

In a fifteenth aspect, in addition to one or more of the preceding or following aspects, or in the alternative to some aspects, the ear-worn device or an accessory device in communication therewith can be further configured to initiate a protective countermeasure if exposure is anticipated to cross an instantaneous threshold value or a defined time total of exposure threshold value.

In a sixteenth aspect, in addition to one or more of the preceding or following aspects, or in the alternative to some aspects, the protective countermeasure can include at least one of adjusting at least one of a sound output volume and a frequency filtering setting of the ear-worn device, issuing a command to a sound-emitting device to reduce sound volume, opening or closing an acoustic vent regulation apparatus, initiating administration of an active agent to the ear-worn device wearer, initiating a noise-cancellation feature, and guiding or directing the ear-worn device wearer to a different physical location.

In a seventeenth aspect, in addition to one or more of the preceding or following aspects, or in the alternative to some aspects, guiding or directing the ear-worn device wearer to a different physical location includes guiding or directing the ear-worn device wearer to a physical location that is less noisy than the current physical location.

In an eighteenth aspect, in addition to one or more of the preceding or following aspects, or in the alternative to some aspects, guiding or directing the ear-worn device wearer to a different physical location includes providing a virtual audio guidance beacon.

In a nineteenth aspect, in addition to one or more of the preceding or following aspects, or in the alternative to some aspects, the active agent can include an antioxidant.

In a twentieth aspect, in addition to one or more of the preceding or following aspects, or in the alternative to some aspects, the active agent can include at least one of N-acetylcysteine (NAC), acetyl-L-carnitine, magnesium (Mg2+), glutathione selenium, seglutathione peroxidase, beta-carotene (BC), vitamin A, vitamin E, trolox, tocotrienols, tocopherols, stereoisomers, alpha-lipoic acid, coenzyme Q10, cysteine, a decongestant, saturated hydrogen saline, and fludrocortisone.

In a twenty-first aspect, in addition to one or more of the preceding or following aspects, or in the alternative to some aspects, the ear-worn device or an accessory device in communication therewith can be further configured to receive an input regarding a susceptibility factor of the ear-worn device wearer.

In a twenty-second aspect, in addition to one or more of the preceding or following aspects, or in the alternative to some aspects, the susceptibility factor can include at least one of a medical condition, enlarged vestibular aqueduct (EVA), noise-induced hearing loss, family medical history, genetic testing results, ototoxic medication use, and exposure to cigarette smoke.

In a twenty-third aspect, in addition to one or more of the preceding or following aspects, or in the alternative to some aspects, the medical condition selected from the group consisting of enlarged vestibular aqueduct (EVA), diabetes, heart disease, cancer, congenital ear deformities, albinism, and tinnitus.

In a twenty-fourth aspect, in addition to one or more of the preceding or following aspects, or in the alternative to some aspects, the tracked exposure to hearing degrading conditions can include head movement crossing a threshold value.

In a twenty-fifth aspect, in addition to one or more of the preceding or following aspects, or in the alternative to some aspects, the tracked exposure to hearing degrading conditions can include air pressure changes crossing a threshold value.

In a twenty-sixth aspect, in addition to one or more of the preceding or following aspects, or in the alternative to some aspects, the ear-worn device or an accessory device in communication therewith can be configured to adjust settings of the ear-worn device based on the tracked exposure to hearing degrading conditions.

In a twenty-seventh aspect, in addition to one or more of the preceding or following aspects, or in the alternative to some aspects, the ear-worn device or an accessory device in communication therewith can be configured to adjust settings of the ear-worn device based on anticipated exposure to hearing degrading conditions.

In a twenty-eighth aspect, in addition to one or more of the preceding or following aspects, or in the alternative to some aspects, the stored data regarding tracked exposure further includes contributions to exposure provided by the ear-worn device itself.

In a twenty-ninth aspect, in addition to one or more of the preceding or following aspects, or in the alternative to some aspects, the ear-worn device or an accessory device in communication therewith can be configured to output stored data regarding tracked exposure to an electronic medical record or other health-information related database.

In a thirtieth aspect, in addition to one or more of the preceding or following aspects, or in the alternative to some aspects, the ear-worn device or an accessory device in communication therewith can be configured to store data regarding tracked exposure longitudinally.

In a thirty-first aspect, in addition to one or more of the preceding or following aspects, or in the alternative to some aspects, the ear-worn device or an accessory device in communication therewith can be further configured to determine a direction of a predominant source of noise in an environment and direct the device wearer to orient themselves in order to reduce and/or attenuate exposure.

In a thirty-second aspect, in addition to one or more of the preceding or following aspects, or in the alternative to some aspects, the ear-worn device or an accessory device in communication therewith can be further configured to determine a direction of a predominant source of noise in an environment and direct the device wearer to orient themselves such that the predominant noise source is located in the direction of the ear-worn device's directional microphone null.

In a thirty-third aspect, an ear-worn device is included having a control circuit, a microphone in electrical communication with the control circuit, an electroacoustic transducer for generating sound in electrical communication with the control circuit, and a power supply circuit in electrical communication with the control circuit, wherein the ear-worn device is configured to track exposure to conditions which can degrade hearing in an ear-worn device wearer having an enlarged vestibular aqueduct (EVA) over time via at least one of the microphone and a sensor package. In various embodiments the ear-worn device is configured to store data regarding the tracked exposure. In various embodiments the sensor package includes at least one of a motion sensor and a pressure sensor.

In a thirty-fourth aspect, in addition to one or more of the preceding or following aspects, or in the alternative to some aspects, the tracked exposure to conditions which can degrade hearing in an ear-worn device wearer having an enlarged vestibular aqueduct (EVA) over time can include head movement crossing a threshold value.

In a thirty-fifth aspect, in addition to one or more of the preceding or following aspects, or in the alternative to some aspects, the tracked exposure to conditions which can degrade hearing in an ear-worn device wearer having an enlarged vestibular aqueduct (EVA) over time can include a detected head impact.

In a thirty-sixth aspect, in addition to one or more of the preceding or following aspects, or in the alternative to some aspects, the tracked exposure to conditions which can degrade hearing in an ear-worn device wearer having an enlarged vestibular aqueduct (EVA) over time can include air pressure changes crossing a threshold value.

In a thirty-seventh aspect, in addition to one or more of the preceding or following aspects, or in the alternative to some aspects, the ear-worn device or an accessory device in communication therewith can be further configured to issue a warning if the tracked exposure crosses an instantaneous threshold value or a defined time total exposure threshold value.

In a thirty-eighth aspect, in addition to one or more of the preceding or following aspects, or in the alternative to some aspects, the warning can be provided as at least one of an audible warning, a visual warning, and a haptic warning.

In a thirty-ninth aspect, in addition to one or more of the preceding or following aspects, or in the alternative to some aspects, the warning can be provided to at least one of the ear-worn device wearer and a third party.

In a fortieth aspect, in addition to one or more of the preceding or following aspects, or in the alternative to some aspects, the ear-worn device or an accessory device in communication therewith can be further configured to issue preventative instructions to the ear-worn device wearer or a third party if the tracked exposure crosses an instantaneous threshold value or a defined time total of exposure threshold value.

In a forty-first aspect, in addition to one or more of the preceding or following aspects, or in the alternative to some aspects, the ear-worn device or an accessory device in communication therewith can be further configured to issue preventative instructions to the ear-worn device wearer or a third party if anticipated exposure crosses an instantaneous threshold value or a defined time total of exposure threshold value.

In a forty-second aspect, in addition to one or more of the preceding or following aspects, or in the alternative to some aspects, the ear-worn device or an accessory device in communication therewith can be further configured to recognize an activity of the ear-worn device wearer and issue preventative instructions to the ear-worn device wearer or a third party if the recognized activity is one presenting risk crossing a threshold value.

In a forty-third aspect, in addition to one or more of the preceding or following aspects, or in the alternative to some aspects, the preventative instructions can be provided as at least one of an audible warning, a visual warning, and a haptic warning.

In a forty-fourth aspect, in addition to one or more of the preceding or following aspects, or in the alternative to some aspects, the ear-worn device or an accessory device in communication therewith can be further configured to initiate a protective countermeasure if the tracked exposure crosses an instantaneous threshold value or a defined time total of exposure threshold value.

In a forty-fifth aspect, a method of monitoring hearing loss progression is included, the method including tracking exposure to hearing degrading conditions over time with an ear-worn device, storing data regarding the tracked exposure, and performing at least one of issuing a warning when the tracked exposure crosses an instantaneous threshold value or a defined time total of exposure threshold value, issuing preventative instructions to the ear-worn device wearer when the tracked exposure crosses an instantaneous threshold value or a defined time total exposure threshold value, and initiating a protective countermeasure when the tracked exposure crosses an instantaneous threshold value or a defined time total of exposure threshold value.

In a forty-sixth aspect, in addition to one or more of the preceding or following aspects, or in the alternative to some aspects, the ear-worn device of the method can include a control circuit, a microphone in electrical communication with the control circuit, an electroacoustic transducer for generating sound in electrical communication with the control circuit, a power supply circuit in electrical communication with the control circuit, and a sensor package can include at least one of a motion sensor, an oximeter, a glucometer, an air pressure sensor, a heart rate sensor, a blood pressure sensor, and an ambient air chemical sensor.

In a forty-seventh aspect, in addition to one or more of the preceding or following aspects, or in the alternative to some aspects, the method can further include issuing a warning when the tracked exposure crosses a dynamic threshold based upon a time period's combined exposure intensity and duration.

In a forty-eighth aspect, in addition to one or more of the preceding or following aspects, or in the alternative to some aspects, the method can further include issuing a warning when the tracked exposure crosses an instantaneous threshold value or a defined time total of exposure threshold value.

In a forty-ninth aspect, in addition to one or more of the preceding or following aspects, or in the alternative to some aspects, the method can further include issuing preventative instructions to the ear-worn device wearer of a third party when the tracked exposure crosses an instantaneous threshold value or a defined time total exposure threshold value.

In a fiftieth aspect, in addition to one or more of the preceding or following aspects, or in the alternative to some aspects, can further include predicting when an ear-worn device wearer will cross a threshold value.

In a fifty-first aspect, in addition to one or more of the preceding or following aspects, or in the alternative to some aspects, can further include predicting when an ear-worn device wearer will cross a threshold value based on prior exposure data.

In a fifty-second aspect, in addition to one or more of the preceding or following aspects, or in the alternative to some aspects, can further include sending a prediction of when an ear-worn device wearer will cross a threshold value to an employer.

In a fifty-third aspect, in addition to one or more of the preceding or following aspects, or in the alternative to some aspects, can further include issuing preventative instructions to the ear-worn device wearer or a third party when exposure is anticipated to cross an instantaneous threshold value or a defined time total of exposure threshold value.

In a fifty-fourth aspect, in addition to one or more of the preceding or following aspects, or in the alternative to some aspects, can further include initiating a protective countermeasure when the tracked exposure crosses an instantaneous threshold value or a defined time total of exposure threshold value.

In a fifty-fifth aspect, in addition to one or more of the preceding or following aspects, or in the alternative to some aspects, can further include guiding or directing the ear-worn device wearer to a physical location that is less noisy than the current physical location.

In a fifty-sixth aspect, in addition to one or more of the preceding or following aspects, or in the alternative to some aspects, can further include adjusting settings of the ear-worn device based on the tracked exposure to hearing degrading conditions.

In a fifty-seventh aspect, in addition to one or more of the preceding or following aspects, or in the alternative to some aspects, can further include adjusting settings of the ear-worn device based on anticipated exposure to hearing degrading conditions.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As described above, exposure to various conditions can degrade hearing over time. While this is a problem for all people, it is particularly important for those who already have degrees of hearing loss to preserve the hearing function they still have.

Hearing degradation due to exposure to noise is not simply a matter of noise volume. Rather, with some exceptions such as volume exceeding a very high threshold, damaging effects are generally a function of both volume and the length of time of exposure.

In accordance with embodiments herein, exposure to hearing degrading conditions can be tracked. Hearing degrading conditions that can be tracked herein go beyond just noise volumes and times of exposure. Hearing degrading conditions herein can also include exposure to damaging vibrations (e.g., including, but not limited to, sub-sonic vibrations such as those <20 Hz). Hearing degrading conditions herein can also include exposure to air-borne contaminants that may result in degraded hearing. Hearing degrading conditions herein can also include exposure to ingested or injected contaminants that may result in degraded hearing (including, but not limited to, ototoxic medications such as NSAIDS, aminoglycosides, diuretics, quinine, cisplatin, etc.). Hearing degrading conditions that can be tracked herein can also include head movements (and/or engagement in activities likely to lead to such head movements) of a sufficient magnitude that may result in hearing damage to susceptible individuals.

Further, in various embodiments herein, notifications can be provided to a device wearer and/or a third party when tracked exposure crosses a threshold value, when a threshold value of exposure for a given time period is soon to be reached, and/or when a threshold value of exposure for a given time period is predicted to be reached.

Further, in various embodiments herein, system and/or devices can suggest and/or initiate a protective countermeasure if the tracked exposure crosses a threshold value.

Figure 1:
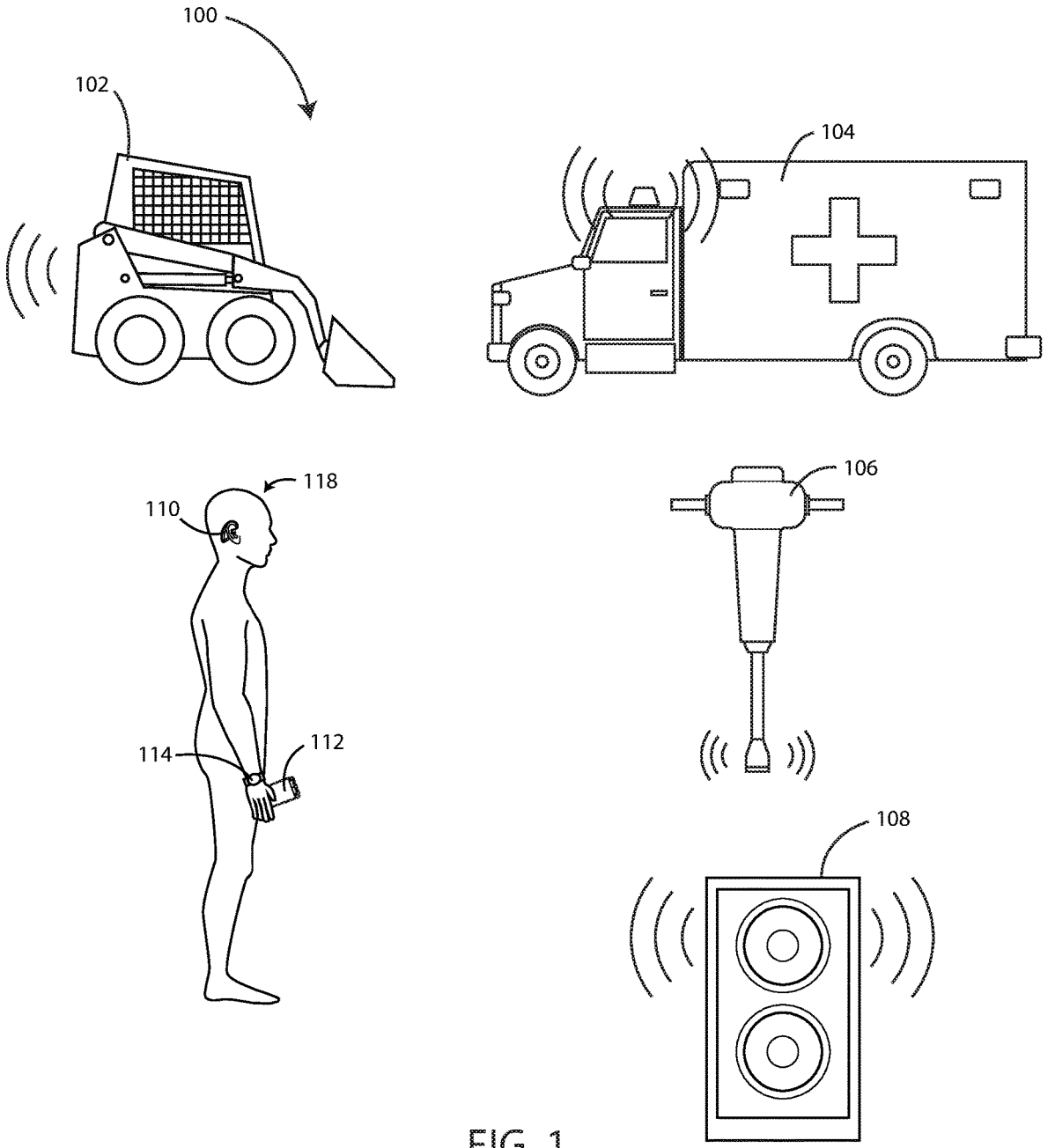
FIG. 1 is a schematic view of an environment including an ear-worn device wearer in accordance with various embodiments herein.

Referring now to FIG. 1, a schematic view of an environment 100 including an ear-worn device wearer 118 is shown in accordance with various embodiments herein. The ear-worn device wearer 118 is wearing an ear-worn device 110. FIG. 1 also shows the ear-worn device wearer 118 with a wearable device 114. FIG. 1 also shows the ear-worn device wearer 118 with an accessory device 112 (which could be, for example, a personal communications device such as a smart phone or the like). In various embodiments herein, the ear-worn device 110 can interface with other devices such as other ear-worn devices, a wearable device 114, or an accessory device 112, or the like.

In this exemplary environment, many sources of potentially harmful noise are shown by way of illustration. For example, the environment 100 includes a piece of diesel equipment 102 (which could also be another type of large piece of machinery). The diesel equipment 102 may generate a significant amount of noise. The environment 100 also includes a truck 104. Trucks can generate a substantial amount of noise and, in some cases, can include other equipment thereon, such as sirens, that generate a substantial amount of noise. In this view, the environment 100 also includes a piece of construction equipment 106. In this example, the piece of construction equipment 106 is shown as a jack hammer creating substantial noise. However, it will be appreciated that many other pieces of construction equipment may create substantial noise. In this example, the environment 100 also includes a loud speaker 108. The loud speaker 108 could be in a home, work, or recreational environment and can create substantial noise.

In various embodiments, the ear-worn device 110 can be configured to track exposure to hearing degrading conditions over time via a microphone and/or a sensor package. In various embodiments, the ear-worn device 110 can be configured to store data (and/or transfer data for storage) regarding the tracked exposure. The tracked exposure can relate to noise volumes and times of exposure, but can also include (in addition or in replacement) other aspects of exposure such as exposure to damaging vibrations, exposure to airborne contaminants, head movements (such as sudden, jarring head movements), engagement in activities that are likely to include such head movements, and the like.

Exposure can be tracked in various ways. In some embodiments (such as in the case of simply tracking exposure to noise), exposure can be tracked according to signals from microphone(s) associated with ear-worn devices 110 herein. In some embodiments, exposure can be tracked according to ANSI S3.44 (Determination of Occupational Noise Exposure and Estimation of Noise-Induced Hearing Impairment). In some embodiments, exposure can be tracked according to OSHA Standard Number 1910.95 App A (Noise Exposure Computation). In some embodiments, exposure can be tracked according to Canadian standard Z107.56-13 (2013) (Measurement of Noise Exposure—Canadian Standards Association).

Exposure herein can also include contributions from or coming through the ear-worn device itself. For example, ear-worn devices herein may amplify and/or otherwise process and deliver sound for the benefit of a device wearer with degraded hearing acuity. As another example, the ear-worn device can provide streamed audio to the device wearer. While the audio provided by the ear-worn device is controlled so as to be not harmful, it may nonetheless contribute to the overall amount of exposure that the device wearer receives. Thus, in various embodiments herein, the sound/audio provided to the device wearer by the ear-worn device is included when tracking exposure. In some embodiments, the sound/audio provided to the device wearer can be simply treated as being additive to other noise/sound that the device wearer is exposed to.

In some embodiments, characteristics of the hearing device's acoustic venting can be factored into calculations of exposure. For example, ear molds and in-ear devices can prevent some external sounds from reaching the eardrum of the wearer. Ear molds and in-ear devices that play sound in the ear may also leak sound from the ear in proportion to the amount of acoustic venting. Parameters relating to the degree of acoustic venting can be manually programmed specific to each device or calculated based upon measurements of the acoustic feedback path, wherein sounds played by the ear-worn device can reach the microphone of the ear-worn device in a feedback loop.

In some embodiments, the acoustic venting may be minimal, but external sounds can be of a magnitude great enough to reach the inner ear via the bone conduction pathway through vibrations of the user's skull. As such, sounds exceeding the bone-conduction threshold level can be factored into calculations which may include various amounts of acoustic venting.

In various embodiments, the ear-worn device 110 can be further configured to issue a warning if the tracked exposure (for any of the elements that are tracked or a combination thereof) crosses a threshold. In various embodiments, the warning is provided as at least one of an audible warning, a visual warning, and a haptic warning. In various embodiments, the warning is provided to at least one of the ear-worn device wearer 118 and a third party (as described further below).

Many different types of threshold values are contemplated herein. In various embodiments, the ear-worn device 110 can be further configured to issue a warning if the tracked exposure crosses a threshold based upon a fixed time combined exposure intensity and duration. For example, the ear-worn device can be configured to issue a warning if the tracked exposure crosses a threshold value for a 24-hour period of combined exposure intensity and duration. It will be appreciated that other time periods are also contemplated herein such as 60 seconds, 5 minutes, 10 minutes, 30 minutes, 1 hour, 2 hours, 4 hours, 6 hours, 8 hours, 12 hours, 18 hours, 24 hours, 48 hours, 1 week, 1 month, 3 months, 6 months, 9 months, 12 months, 5 years, or a time period falling within a range between any of the foregoing. In some embodiments, thresholds herein can correspond with OSHA and NIOSH safe-exposure limits. In various embodiments, if variations in noise level involve maxima at intervals of one second or less, it can be considered to be considered continuous for purposes of calculating the total amount of exposure time.

In various embodiments, the ear-worn device 110 can be further configured to issue a warning if the tracked exposure specifically crosses a dynamic threshold. A threshold can be dynamic in the sense that the value to compare with it is multi-factorial, such as based upon combined exposure intensity and duration. For example, the value to compare against a dynamic threshold (Tr) can be calculated according to the following equation:

$$\text{Value} = (r_1 * \text{volume}_{RMS}) + (r_2 * t)$$

wherein $r_1$ is a volume weighting parameter, $\text{volume}_{RMS}$ is the root mean square (RMS) volume over time period t and $r_2$ is the time weighting parameter. In its simplest form, $r_1$ and $r_2$ may simply be equal to 1. However, in some other embodiments, $r_1$ and $r_2$ may be, independently, about 0.001 to 10, such as 0.001, 0.01, 0.1, 0.2, 0.3, 0.4, 0.5, 0.75, 1, 1.5, 2, 2.5, 3, 3.5, 4, 5, 6, 7, 8, 9, or 10, or a value falling within a range between any of the foregoing. While the RMS value of volume is used in this example, it will be appreciated that there are various other ways of evaluating volume including various mathematical and statistical methods such as maximums during a time period, minimums during a time period, mathematical averages (mean, median, mode), statistical measures including deviations, moving averages, and the like. It will be appreciated that calculations may apply specific weightings to intensity measurement values obtained in one or more frequency bands, using any suitable scale (e.g., A-weighting, C-weighting, and the like). Further, it will be appreciated that volume (such as when measured in decibels) is not a linear scale. Therefore, in some embodiments, the root value of volumes can be used for calculations herein. By way of example, some embodiments can utilize the following equation or variants thereof:

$$\text{Value} = \sqrt{\text{volume}_{RMS}} * r_3 * t)$$

wherein the variables in this equation are as described above, but $r_3$ is a scaling parameter.

In some embodiments, a dynamic threshold can correspond to exposure guidelines set by OSHA and/or NIOSH as shown below in Table 1, wherein "PEL" stands for Permissible Exposure Limit, "REL" stands for Recommended Exposure Limit, and the duration is in hours.

TABLE 1

| | Volume—dB A | | | | | | | | | |
|---|---|---|---|---|---|---|---|---|---|---|
| | 85 | 88 | 90 | 92 | 94 | 95 | 100 | 105 | 110 | 115 |
| OSHA PEL | 16 | | 8 | | | 4 | 2 | 1 | 0.5 | 0.25 |
| NIOSH REL | 8 | 4 | | | 1 | | 0.25 | | | |

In some embodiments, thresholds herein can correspond to those provided in 29 C.F.R. § 1910.95.

In various embodiments, the ear-worn device 110 can be further configured to issue a warning if the tracked exposure crosses an instantaneous threshold value or a defined time total of exposure threshold value. An instantaneous threshold can be, for example, exposure to noise that crosses a threshold value, regardless of the time of exposure. For example, in some cases, exposure to noise having a volume of greater than 70, 75, 80, 85, 90, 95, 100, 105, 110, 115, 120, 130, 140 or more can qualify as an instantaneous threshold (or a value falling within a range between any of the foregoing) because detection of such a noise volume will instantly qualify as exceeding the threshold.

In some embodiments, the threshold value can be a defined time total of exposure to at least some minimum volume of noise (which can be evaluated as the RMS volume or any of the other types of measures discussed above). As such, for every unit of time (millisecond, second, minute, hour, etc.) that the minimum volume of noise is detected, the total exposure time is incremented upward accordingly and then compared with the threshold value for total time. As just one specific example, for every second that noise volume exceeds 70 dB A a time counter is incremented upward and when the time counter reaches 60 minutes, the threshold is determined to have been met. For such purposes, the noise volume minimum can be greater than or equal to 50, 55, 60, 65, 70, 75, 80, 85, 90, 95, or 100 dB A, or a range falling between any of the foregoing. The threshold time in such cases can be, for example, 10 minutes, 30 minutes, 1 hour, 2 hours, 4 hours, 6 hours, 8 hours, or an amount of time falling within a range between any of the foregoing.

In various embodiments, the ear-worn device 110 can be further configured to issue preventative instructions to the ear-worn device wearer 118 if the tracked exposure crosses a threshold value. Further details regarding exemplary preventative instructions are provided in greater detail below.

In various embodiments, the ear-worn device 110 can be further configured to initiate a protective countermeasure if the tracked exposure crosses a threshold value. Further details regarding protective countermeasures are provided in greater detail below.

In various embodiments, the ear-worn device 110 is configured to predict a future time when an ear-worn device wearer 118 will cross a threshold value based on one or more of current and prior exposure data of one or more users of the system. Further details regarding operations associated with predication are described in greater detail below.

As described above, the tracked exposure is not just limited to volumes of noise and time of exposure in some embodiments. In various embodiments, the tracked exposure to hearing degrading conditions can include head movement crossing a threshold value. As described elsewhere herein, individuals with EVA (enlarged vestibular aqueduct) as susceptible to hearing degradation from sudden movements, acceleration, or impacts which may occur as a part of everyday life or may occur resulting from participation in sports or other recreational activities. Sensors used with embodiments herein can include accelerometers (as described further below) that can measure head acceleration. In some embodiments, exposure can be tracked much as with noise described above, but instead of noise (or in addition to noise) tracking head movement, acceleration, and/or impacts. In some embodiments, exemplary thresholds for tracking forces associated with movement, acceleration, and/or impacts can be about 10, 20, 30, 40, 50, 60, 70, 80, 90, 100, 110, or 120 g's, or an amount falling within a range between any of the foregoing. In some embodiments, tracked exposure to head movements can be tracked as the number of events observed exceeding the threshold over a given interval of time.

In various embodiments, the tracked exposure to hearing degrading conditions can include air pressure changes crossing a threshold value. In some embodiments, exemplary thresholds for tracking forces associated with air pressure changes can be about 10, 20, 30, 40, 50, 75, 100, 125, 150, 175, 200, 250, or 300 mmHg or an amount falling within a range between any of the foregoing.

Various pieces of data regarding tracked exposure can be stored. By way of example, sound volume or vibration exposure, duration of exposure, and at least one of concurrent movement, concurrent position, concurrent oxygen saturation, concurrent blood glucose concentrations, concurrent heart rate, concurrent blood pressure, and concurrent ambient air chemical sensor data can all be stored herein.

In various embodiments, stored data regarding tracked exposure can include sound volume or vibration exposure, duration of exposure, and a risk index factor calculated using at least one of concurrent movement, concurrent position, concurrent oxygen saturation, concurrent blood glucose concentrations, concurrent heart rate, concurrent blood pressure, concurrent ambient air chemical sensor data, and sound or vibration exposure during a preceding time period.

In various embodiments, data regarding tracked exposure can be output to an electronic medical record or other health-information related database. For example, data regarding exposure gathered herein can be sent through a data network to an electronic medical record system. In various embodiments herein, systems and/or devices described herein can use an API (application programming interface) for an electronic medical record system in order to securely upload information regarding exposure of the device wearer. In various embodiments herein, systems and/or devices described herein can upload information regarding exposure of the device wearer to an employer's safety record keeping system.

In various embodiments herein, data regarding tracked exposure can be stored for purposes of longitudinal analysis of an ear-worn device wearer and/or a population of ear-worn device wearers. By way of example, data regarding tracked exposure can be stored representing a period of time of at least 5, 10, 15, 30, 45, 60, 90, 120, 180, 270, 365 days, 2 years, or longer. Exposure over such period of time can also be analyzed using statistical analysis including, for example, calculating averages, standard deviations, trends including moving averages, and the like. In some embodiments, longitudinal tracked exposure data herein can be provided to a clinician or other healthcare professional, an employer, or another third party. It will be appreciated that a correlation exists between noise exposure and stress. In turn, stress impacts many chronic health conditions including those in the categories of cardiovascular health, mental health, and the like. Thus, longitudinal data on noise exposure is an extremely valuable data set for purposes of evaluating a device wearer's overall current health state and anticipated future health state. As such, in accordance with various embodiments herein, data regarding longitudinal noise exposure can be evaluated (and/or can be provided to another system) for purposes of evaluating stress that a device wearer is subjected to over time. In various embodiments herein, other data gathered with sensors herein (and particularly that related to stress) can also be stored and then provided/used for longitudinal analysis including, but not limited to, heart rate sensor data, blood pressure sensor data, temperature sensor data, and/or data regarding mood and/or emotion (such as gathered through evaluation of voice samples or other audio data, aspects of which are described in U.S. Pat. Appl. No. 62/800,227, the content of which is herein incorporated by reference).

In various embodiments, the ear-worn device 110 (or another component herein) can further be configured to adjust one or more settings of the ear-worn device 110 based on the tracked exposure to hearing degrading conditions. In various embodiments, the ear-worn device (or another component herein) can further be configured to adjust one or more settings of the ear-worn device 110 based on anticipated exposure to hearing degrading conditions. In various embodiments, the ear-worn device (or another component herein) can further be configured to adjust one or more settings and operations (e.g., by issuing a command to a sound-emitting device to reduce sound volume, or the like) of a noise source (which could be any of the noise sources shown in FIG. 1, as well as other types of controllable noise sources) based on one or more user's anticipated exposure to hearing degrading conditions. Anticipated exposure can include aspects of analysis and calculation as described below with respect to prediction of timing for crossing thresholds. By way of example, overall anticipated exposure can include anticipated exposure contributions from work schedules, exposure based on time of day, exposure from calendared/scheduled events (such as determined from an electronic calendar data, reminder data, data regarding event tickets/passes, social media data, personal correspondence data), and the like. In some examples, social media, personal correspondence, calendar data and reminder data can include data indicating appointments and/or anticipated locations of the device wearer that can be processed to determine anticipated exposure contributions.

Figure 2:
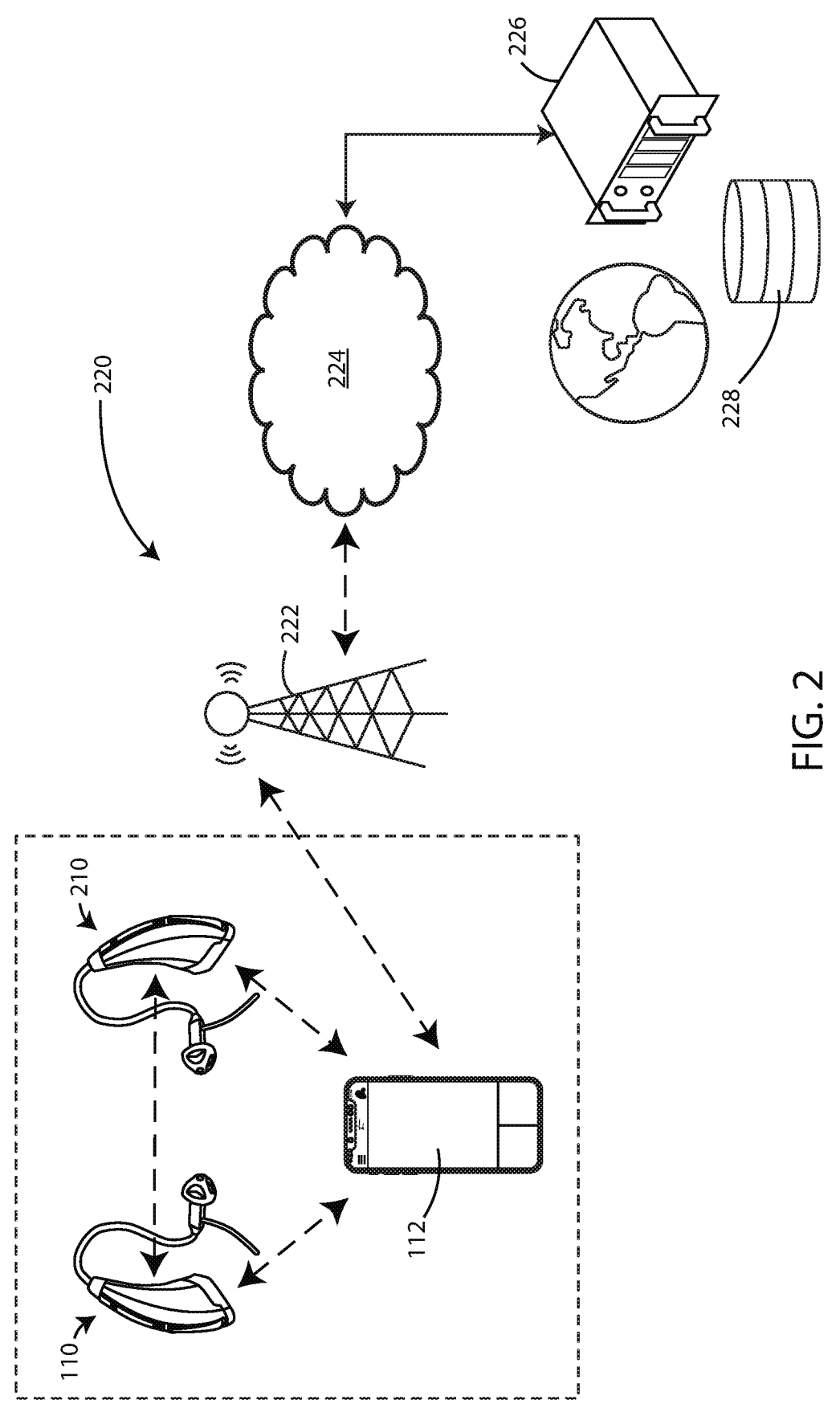
FIG. 2 is a schematic view of a data communication network in accordance with various embodiments herein.

Referring now to FIG. 2, a schematic view of a data communication network 220 associated with ear-worn devices is shown in accordance with various embodiments herein. FIG. 2 shows an ear-worn device 110 and a second ear-worn device 210. The ear-worn device 110 and the second ear-worn device 210 can be in communication with an accessory device 112. The data communication network 220 can, in some cases, include a cell tower 222. The data communication network 220 can, in some cases, include a mesh network of devices or the Internet of Things (IoT). However, in various embodiments, it will be appreciated that there are other ways for the ear-worn device 110 to connect to a data network. The data communication network 220 includes the cloud 224. In this view, the data communication network 220 can also include a server 226 (real or virtual). In some embodiments, the server 226 may itself be considered to be a part of the cloud 224. In other embodiments, the server 226 may be reachable through the cloud 224. The data communication network 220 also includes a database 228. In some embodiments, the database 228 may itself be considered to be a part of the cloud 224. In other embodiments, the database 228 may be reachable through the cloud 224.

Various embodiments herein can include the use of an accessory device. Accessory devices herein can be in communication with the ear-worn device(s). The accessory devices can be useful for various aspects including, but not limited to, as a bridge or gateway to a data network, as a processing resource that may have more processing power than that associated with the ear-worn device, a means for displaying visual information to the device wearer, as a means for receiving user input, etc.

Figure 3:
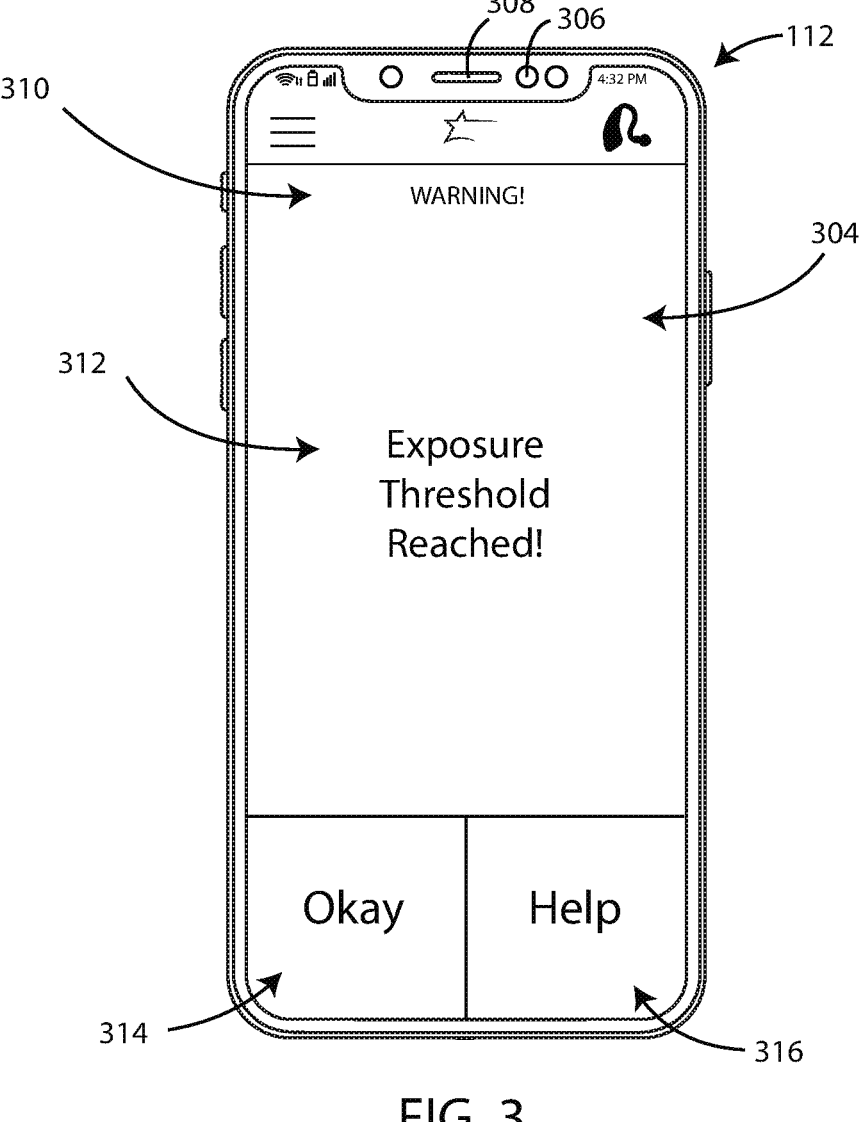
FIG. 3 is a schematic view of an accessory device in accordance with various embodiments herein.

Referring now to FIG. 3, a schematic view of an accessory device 112 is shown in accordance with various embodiments herein. In some embodiments, the accessory device 112 can specifically be a personal communications device.

The accessory device 112 includes a speaker 308. The accessory device 112 also includes a camera 306. The accessory device 112 also includes a display screen 304. Various pieces of information (data, notifications, queries, warnings, instructions, etc.) can be displayed on the display screen 304.

The accessory device 112 can include various user interface features on the display screen 304. By way of example, the accessory device 112 can include a first user interface button 314. The accessory device 112 can also include a second user interface button 316. In this example, the accessory device 112 also includes a warning 310. The accessory device 112 also includes a notification 312. In this case, the ear-worn device wearer can respond to the notification 312 or warning by interfacing with one of the buttons.

While this example shows a visual notification/warning, it will be appreciated that such notifications/warnings etc. can be aural, visual, haptic, or a combination thereof.

In various embodiments, the prompt is delivered through the ear-worn device 110, such as an audio or haptic prompt.

Figure 4:
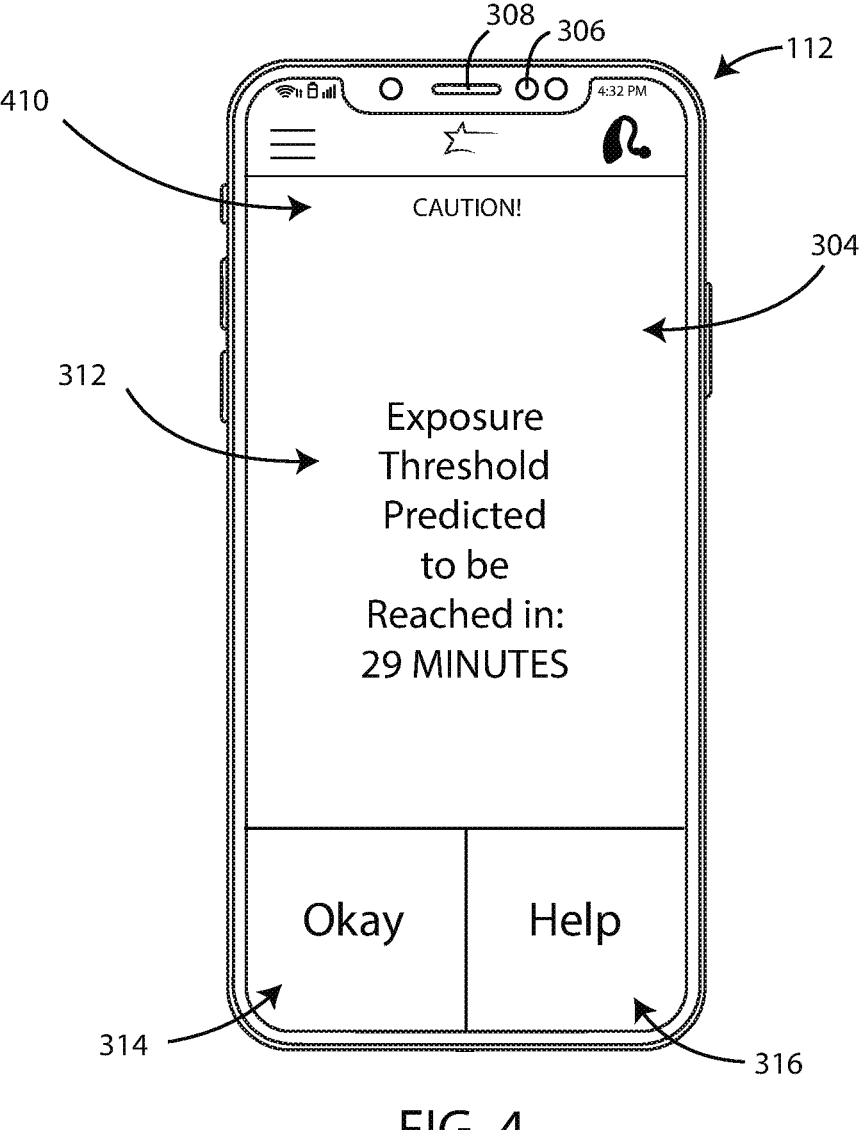
FIG. 4 is a schematic view of an accessory device in accordance with various embodiments herein.

Referring now to FIG. 4, a schematic view of an accessory device 112 is shown in accordance with various embodiments herein. FIG. 4 is generally similar to FIG. 3. However, in FIG. 4 the accessory device 112 displays a caution message 410 and a different notification 312. The notification 312 of FIG. 3 related to a threshold being crossed whereas the notification 312 of FIG. 4 relates to a prediction of when a threshold will be crossed.

In various embodiments, the ear-worn device 110 is further configured to recognize an activity of the ear-worn device wearer 118. Also, in some embodiments, the ear-worn device 110 can issue preventative instructions to the ear-worn device wearer 118 or a third party 504 if the recognized activity is one presenting risk crossing a threshold value.

Figure 5:
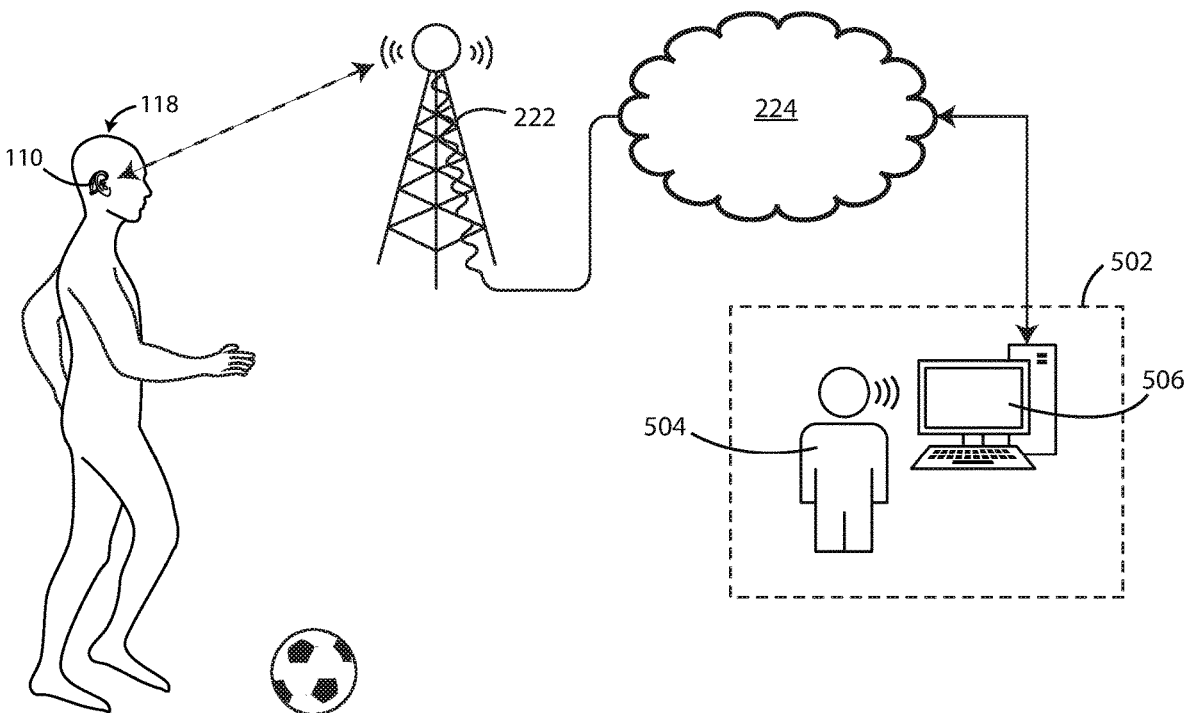
FIG. 5 is a schematic view of an environment including an ear-worn device wearer in accordance with various embodiments herein.

Referring now to FIG. 5, a schematic view of an environment 100 including an ear-worn device wearer 118 is shown in accordance with various embodiments herein. FIG. 5 shows the ear-worn device wearer 118 engaging in a sports activity. Data from accelerometers of the ear-worn device 110 can be sent through a cell tower 222 and into the cloud 224 for processing and, specifically, can be sent to a remote location 502. The remote location 502 can include computing device(s) 506. In some embodiments, a third party 504 can be at the remote location or, at least, can be in electronic communication with the computing resources thereof. Computing resources either in the cloud 224 and/or at the remote location 502 can be used to evaluate the accelerometer data (and/or other sensor data) and determine the type of activity that the ear-worn device wearer is engaging in. It will also be appreciated that computing resources of one or more of the ear-worn device 110 and accessory device 112 can be used to evaluate the accelerometer data (and/or other sensor data) and determine the type of activity that the ear-worn device wearer is engaging in. If the type of activity represents a significant risk to a device wearer (such as if they have EVA), then a notification/warning can be sent to the ear-worn device wearer 118 and/or the third party 504. For example, detected head inversions associated with playing on playground bars may represent a significant risk resulting in a notification/warning to the ear-worn device wearer 118 and/or to a third party 504, which could be a care provider, parent, guardian, physician, clinician, educator, etc.

In various embodiments, the sensor package of an ear-worn device herein can include at least one of a motion sensor, an oximeter, a glucometer, an air pressure sensor, a heart rate sensor, a blood pressure sensor, and an ambient air chemical sensor. However, other sensors are also contemplated herein.

Figure 6:
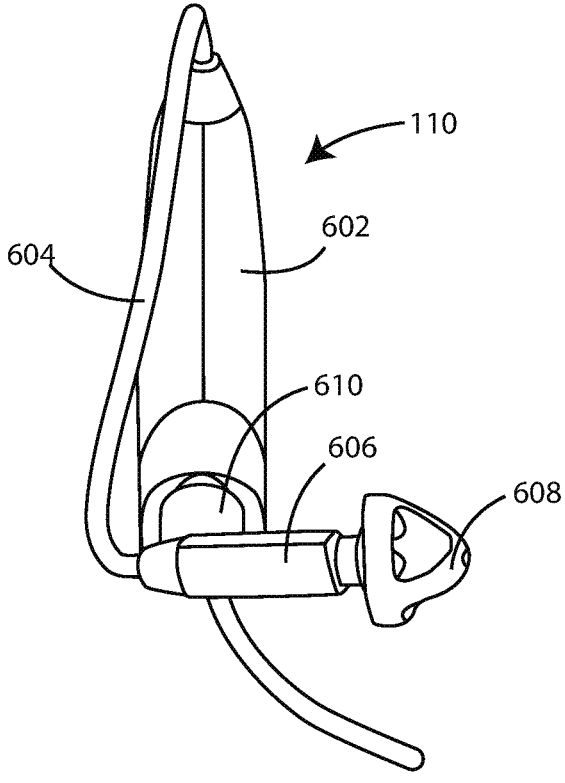
FIG. 6 is a schematic view of an ear-worn device in accordance with various embodiments herein.

Referring now to FIG. 6, a schematic view of an ear-worn device 110 is shown in accordance with various embodiments herein. The ear-worn device 110 can include a hearing device housing 602. The device housing 602 can define a battery compartment 610 into which a battery can be disposed to provide power to the device. The ear-worn device 110 can also include a receiver 606 adjacent to an earbud 608. The receiver 606 an include a component that converts electrical impulses into sound, such as an electroacoustic transducer, speaker, or loud speaker. Such components can be used to generate an audible stimulus in various embodiments herein. A cable 604 or connecting wire can include one or more electrical conductors and provide electrical communication between components inside of the device housing 602 and components inside of the receiver 606.

The ear-worn device 110 shown in FIG. 6 is a receiver-in-canal type device and thus the receiver is designed to be placed within the ear canal. However, it will be appreciated that may different form factors for ear-worn devices are contemplated herein. As such, ear-worn devices herein can include, but are not limited to, behind-the-ear (BTE), in-the ear (ITE), in-the-canal (ITC), invisible-in-canal (IIC), receiver-in-canal (RIC), receiver in-the-ear (RITE) and completely-in-the-canal (CIC) type hearing assistance devices.

The term "ear-worn device" shall also refer to devices that can produce optimized or processed sound for persons with normal hearing. Ear-worn devices herein can include hearing assistance devices. In some embodiments, the ear-worn device can be a hearing aid falling under 21 C.F.R. § 801.420. In another example, the ear-worn device can include one or more Personal Sound Amplification Products (PSAPs). In another example, the ear-worn device can include one or more cochlear implants, cochlear implant magnets, cochlear implant transducers, and cochlear implant processors. In another example, the ear-worn device can include one or more "hearable" devices that provide various types of functionality. In other examples, ear-worn devices can include other types of devices that are wearable in, on, or in the vicinity of the user's ears. In other examples, ear-worn devices can include other types of devices that are implanted or otherwise osseointegrated with the user's skull; wherein the device is able to facilitate stimulation of the wearer's ears via the bone conduction pathway.

Ear-worn devices of the present disclosure can incorporate an antenna arrangement coupled to a high-frequency radio, such as a 2.4 GHz radio. The radio can conform to an IEEE 802.11 (e.g., WIFI®) or BLUETOOTH® (e.g., BLE, BLUETOOTH® 4.2 or 5.0) specification, for example. It is understood that ear-worn devices of the present disclosure can employ other radios, such as a 900 MHz radio. Ear-worn devices of the present disclosure can be configured to receive streaming audio (e.g., digital audio data or files) from an electronic or digital source. Representative electronic/digital sources (also referred to herein as accessory devices) include an assistive listening system, a TV streamer, a radio, a smartphone, a cell phone/entertainment device (CPED) or other electronic device that serves as a source of digital audio data or files.

Figure 7:
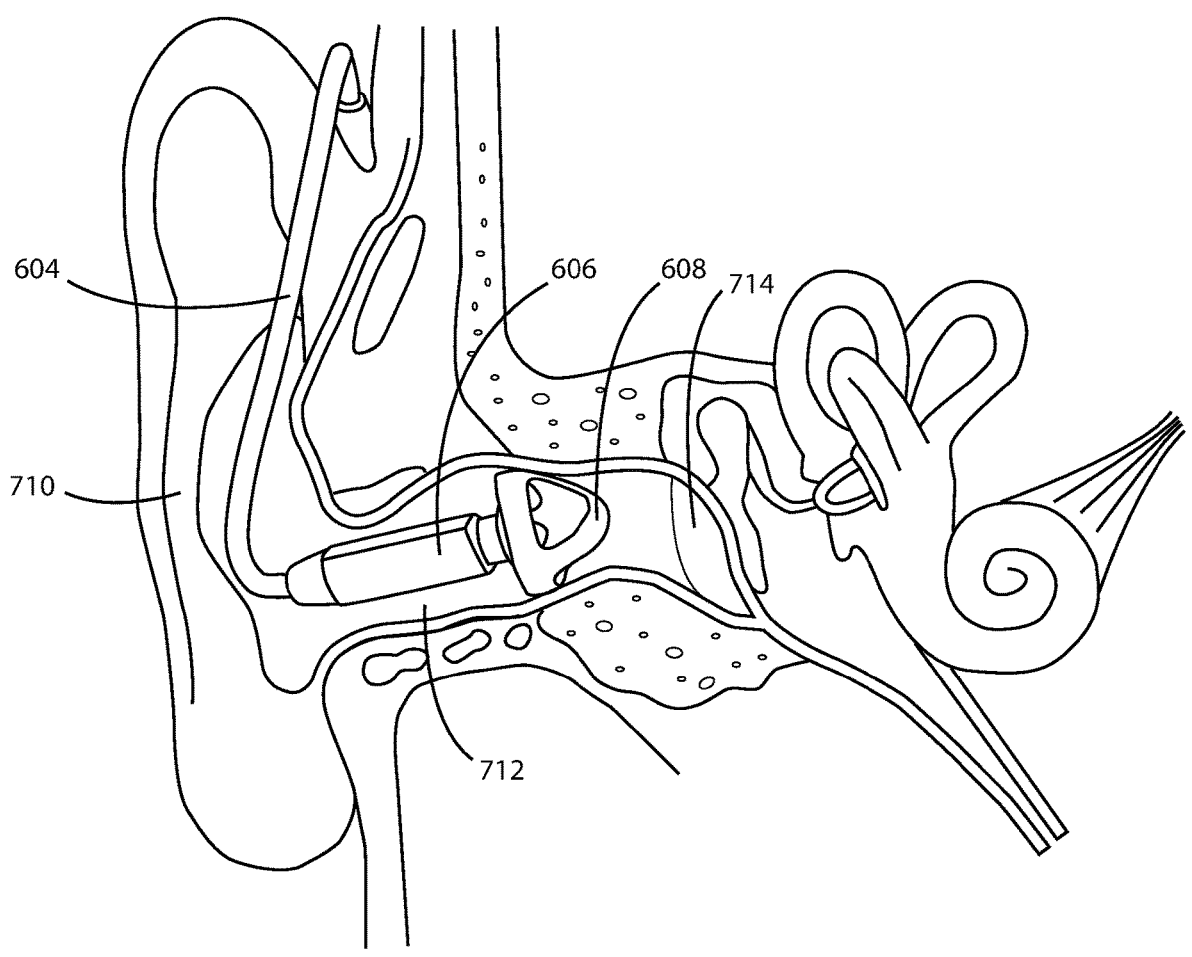
FIG. 7 is a schematic view of an ear-worn device within an ear in accordance with various embodiments herein.

As mentioned above, the ear-worn device 110 shown in FIG. 6 can be a receiver-in-canal type device and thus the receiver is designed to be placed within the ear canal. Referring now to FIG. 7, a schematic view is shown of an ear-worn device 110 disposed within the ear of a subject in accordance with various embodiments herein. In this view, the receiver 606 and the earbud 608 are both within the ear canal 712, but do not directly contact the tympanic membrane 714. The hearing device housing is mostly obscured in this view behind the pinna 710, but it can be seen that the cable 604 passes over the top of the pinna 710 and down to the entrance to the ear canal 712.

Figure 8:
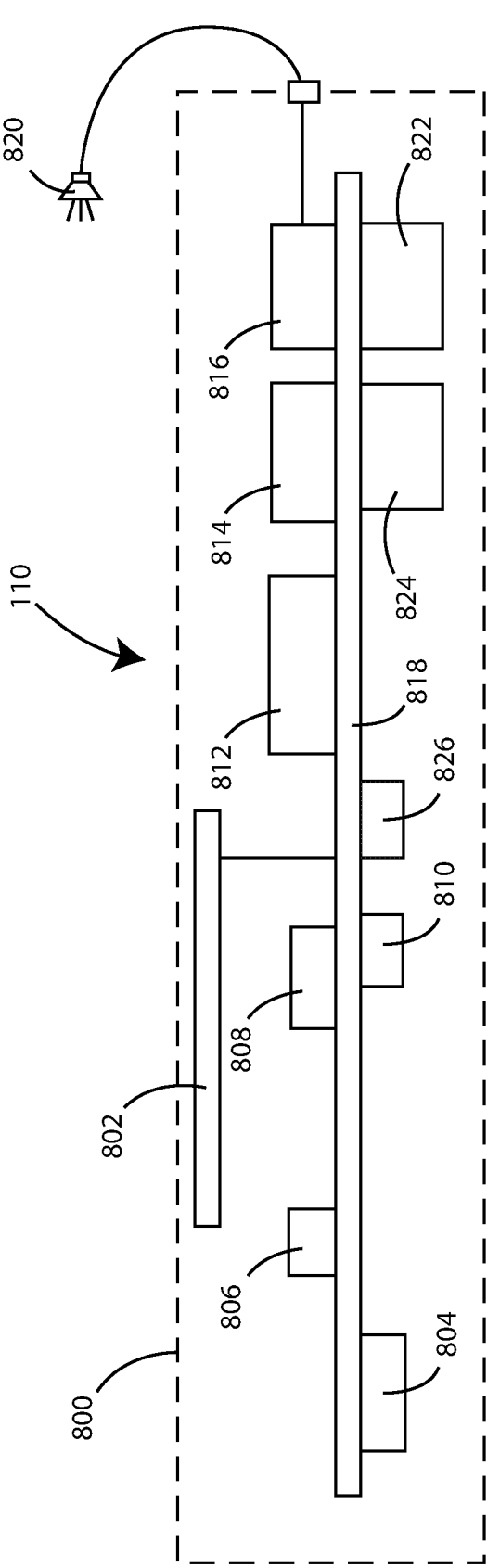
FIG. 8 is a block diagram of components of an ear-worn device in accordance with various embodiments herein.

Referring now to FIG. 8, a schematic block diagram of components of an ear-worn device is shown in accordance with various embodiments herein. The block diagram of FIG. 8 represents a generic ear-worn device for purposes of illustration. The ear-worn device 110 shown in FIG. 8 includes several components electrically connected to a flexible mother circuit 818 (e.g., flexible mother board) which is disposed within housing 800. A power supply circuit 804 can include a battery and can be electrically connected to the flexible mother circuit 818 and provides power to the various components of the ear-worn device 110. One or more microphones 806 are electrically connected to the flexible mother circuit 818, which provides electrical communication between the microphones 806 and a digital signal processor (DSP) 812. Among other components, the DSP 812 incorporates or is coupled to audio signal processing circuitry configured to implement various functions described herein. A sensor package 814 can be coupled to the DSP 812 via the flexible mother circuit 818. The sensor package 814 can include one or more different specific types of sensors such as those described in greater detail below. One or more user switches 810 (e.g., on/off, volume, mic directional settings) are electrically coupled to the DSP 812 via the flexible mother circuit 818.

An audio output device 816 is electrically connected to the DSP 812 via the flexible mother circuit 818. In some embodiments, the audio output device 816 comprises a speaker (coupled to an amplifier). In other embodiments, the audio output device 816 comprises an amplifier coupled to an external receiver 820 adapted for positioning within an ear of a wearer. The external receiver 820 can include an electroacoustic transducer, speaker, or loud speaker. The ear-worn device 110 may incorporate a communication device 808 coupled to the flexible mother circuit 818 and to an antenna 802 directly or indirectly via the flexible mother circuit 818. The communication device 808 can be a BLUETOOTH® transceiver, such as a BLE (BLUETOOTH® low energy) transceiver or other transceiver(s) (e.g., an IEEE 802.11 compliant device). The communication device 808 can be configured to communicate with one or more external devices, such as those discussed previously, in accordance with various embodiments. In various embodiments, the communication device 808 can be configured to communicate with an external visual display device such as a smart phone, a video display screen, a tablet, a computer, virtual reality device, augmented reality device, or the like.

In various embodiments, the ear-worn device 110 can also include a control circuit 822 and a memory storage device 824. The control circuit 822 can be in electrical communication with other components of the device. In some embodiments, a clock circuit 826 can be in electrical communication with the control circuit. The control circuit 822 can execute various operations, such as those described herein. The control circuit 822 can include various components including, but not limited to, a microprocessor, a microcontroller, an FPGA (field-programmable gate array) processing device, an ASIC (application specific integrated circuit), or the like. The memory storage device 824 can include both volatile and non-volatile memory. The memory storage device 824 can include ROM, RAM, flash memory, EEPROM, SSD devices, NAND chips, and the like. The memory storage device 824 can be used to store data from sensors as described herein and/or processed data generated using data from sensors as described herein.

It will be appreciated that various of the components described in FIG. 8 can be associated with separate devices and/or accessory devices to the ear-worn device. By way of example, microphones can be associated with separate devices and/or accessory devices. Similarly, audio output devices can be associated with separate devices and/or accessory devices to the ear-worn device.

Methods

Many different methods are contemplated herein, including, but not limited to, methods of making, methods of using, and the like. Aspects of system/device operation described elsewhere herein can be performed as operations of one or more methods in accordance with various embodiments herein.

In an embodiment, a method of monitoring hearing loss progression is included. The method can include tracking exposure to hearing degrading conditions over time with an ear-worn device, storing data regarding the tracked exposure, and performing at least one of issuing a warning if the tracked exposure crosses an instantaneous threshold value or a defined time total of exposure threshold value. The method can further include issuing preventative instructions to the ear-worn device wearer if the tracked exposure crosses an instantaneous threshold value or a defined time total exposure threshold value and initiating a protective countermeasure if the tracked exposure crosses an instantaneous threshold value or a defined time total of exposure threshold value.

In an embodiment, the ear-worn device can include a control circuit, a microphone in electrical communication with the control circuit, an electroacoustic transducer for generating sound in electrical communication with the control circuit, a power supply circuit in electrical communication with the control circuit, and a sensor package. The sensor package can include at least one of a motion sensor, an oximeter, a glucometer, an air pressure sensor, a heart rate sensor, a blood pressure sensor, and an ambient air chemical sensor.

In an embodiment, the method can further include issuing a warning if the tracked exposure crosses a dynamic threshold based upon a time period's combined exposure intensity and duration. The time period can be any given amount of time, for example, a calendar day, a work day, a work shift, a moving window of a certain number of hours (e.g., a moving 24-hour window), a period of minutes, hours, days, etc.

In an embodiment, the method can further include issuing a warning if the tracked exposure crosses an instantaneous threshold value or a defined time total of exposure threshold value.

In an embodiment, the method can further include issuing preventative instructions to the ear-worn device wearer if the tracked exposure crosses an instantaneous threshold value or a defined time total exposure threshold value.

In an embodiment, the method can further include predicting when an ear-worn device wearer will cross a threshold value based on prior exposure data.

In an embodiment, the method can further include initiating a protective countermeasure if the tracked exposure crosses an instantaneous threshold value or a defined time total of exposure threshold value.

In an embodiment, the method can further include guiding or directing the ear-worn device wearer to a physical location that is less noisy than the current physical location. In some embodiments, locations that are less noisy can be identified based on the type of building that is at the location (for example a library or a church are typically quiet places). In some embodiments, locations that are less noisy may be provided based on inputs from a mesh network or an API from which requests regarding less noisy locations can be made. In some embodiments, locations that are less noisy can be determined based on room beacons, data from other users, data from prior data of the same user, and the like.

In some embodiments, guiding and/or directing can be performed by virtue of providing three-dimensional audio (audio that is perceived to emanate from a particular spatial point) guidance to the device wearer. Aspects of three-dimensional audio interfaces are described in U.S. Publ. Appl. No. 2018/0317837.

In various embodiments, the method can further include determining the direction of the predominant noise in an environment (which could be the loudest noise within an environment) and then directing the device wearer to orient themselves (including even the direction of the device wearers head) in order to reduce and/or attenuate exposure. In some embodiments, the ear-worn device can direct the device wearer to orient themselves such that the noise source is located in the direction of the device's directional microphone null (the "null" is an area representing the least sensitive portion of the microphone response—e.g., where the microphone array is least sensitive). As an example, various ear-worn devices herein have the ability to determine the direction of sound sources by measuring frequency filter differences (such as the head shadow effect), measuring interaural time differences, measuring interaural intensity differences, using directional microphones, and the like. Such directional information can be used to provide direction to the device wearer to reorient themselves to attenuate or otherwise modify exposure. In some cases, directional information can be used to cause the device wearer to balance exposure between ears using the natural sound attenuation properties of the head itself "head shadow effect". By way of example, the ear-worn device can issue a command to the device wearer (aurally, visually, or haptically) such as "turn head 90 degrees left" or "turn head 30 degrees right", wherein such positioning results in attenuated and/or more advantageous (such as more balanced) exposure.

In an embodiment, the method can further include adjusting settings of the ear-worn device based on the tracked exposure to hearing degrading conditions. In an embodiment, the method can further include adjusting settings of the ear-worn device based on anticipated exposure to hearing degrading conditions.

Sensors

Ear-worn devices herein can include one or more sensor packages (including one or more discrete or integrated sensors) to provide data. The sensor package can comprise one or a multiplicity of sensors. In some embodiments, the sensor packages can include one or more motion sensors amongst other types of sensors. Motion sensors herein can include inertial measurement units (IMU), accelerometers, gyroscopes, barometers, altimeters, and the like. The IMU can be of a type disclosed in commonly owned U.S. patent application Ser. No. 15/331,230, filed Oct. 21, 2016, which is incorporated herein by reference. In some embodiments, electromagnetic communication radios or electromagnetic field sensors (e.g., telecoil, NFMI, TMR, GME, etc.) sensors may be used to detect motion or changes in position. In some embodiments, biometric sensors may be used to detect body motions or physical activity. Motions sensors can be used to track movement of a patient in accordance with various embodiments herein.

In some embodiments, the motion sensors can be disposed in a fixed position with respect to the head of a patient, such as worn on or near the head or ears. In some embodiments, the operatively connected motion sensors can be worn on or near another part of the body such as on a wrist, arm, or leg of the patient.

According to various embodiments, the sensor package can include one or more of a motion sensor, (e.g., IMU, and accelerometer (3, 6, or 9 axis), a gyroscope, a barometer, an altimeter, a magnetometer, a magnetic sensor, an eye movement sensor, a pressure sensor), an acoustic sensor, a telecoil, a heart rate sensor, a global positioning system (GPS), a barometer, a temperature sensor, a blood pressure sensor, an oxygen saturation sensor, an optical sensor, a blood glucose sensor (optical or otherwise), a galvanic skin response sensor, a cortisol level sensor (optical or otherwise), a microphone, acoustic sensor, an electrocardiogram (ECG) sensor, electroencephalography (EEG) sensor which can be a neurological sensor, eye movement sensor (e.g., electrooculogram (EOG) sensor), myographic potential electrode sensor (EMG), a heart rate monitor, a pulse oximeter, a wireless radio antenna, blood perfusion sensor, hydrometer, sweat sensor, cerumen sensor, air quality sensor, pupillometry sensor, cortisol level sensor, hematocrit sensor, light sensor, image sensor, and the like.

In some embodiments, the sensor package can be part of an ear-worn device. However, in some embodiments, the sensor packages can include one or more additional sensors that are external to an ear-worn device. For example, various of the sensors described above can be part of a wrist-worn or ankle-worn sensor package, or a sensor package supported by a chest strap.

Data produced by the sensor(s) of the sensor package can be operated on by a processor of the device or system.

As used herein the term "inertial measurement unit" or "IMU" shall refer to an electronic device that can generate signals related to a body's specific force and/or angular rate. IMUs herein can include one or more accelerometers and gyroscopes (3, 6, or 9 axis) to detect linear acceleration and a gyroscope to detect rotational rate. In some embodiments, an IMU can also include a magnetometer to detect a magnetic field.

The eye movement sensor may be, for example, an electrooculographic (EOG) sensor, such as an EOG sensor disclosed in commonly owned U.S. Pat. No. 9,167,356, which is incorporated herein by reference. The pressure sensor can be, for example, a MEMS-based pressure sensor, a piezo-resistive pressure sensor, a flexion sensor, a strain sensor, a diaphragm-type sensor and the like.

The temperature sensor can be, for example, a thermistor (thermally sensitive resistor), a resistance temperature detector, a thermocouple, a semiconductor-based sensor, an infrared sensor, or the like.

The blood pressure sensor can be, for example, a pressure sensor. The heart rate sensor can be, for example, an electrical signal sensor, an acoustic sensor, a pressure sensor, an infrared sensor, an optical sensor, or the like.

The oxygen saturation sensor (such as a blood oximetry sensor) can be, for example, an optical sensor, an infrared sensor, or the like.

The electrical signal sensor can include two or more electrodes and can include circuitry to sense and record electrical signals including sensed electrical potentials and the magnitude thereof (according to Ohm's law where V=IR) as well as measure impedance from an applied electrical potential.

It will be appreciated that the sensor package can include one or more sensors that are external to the ear-worn device. In addition to the external sensors discussed hereinabove, the sensor package can comprise a network of body sensors (such as those listed above) that sense movement of a multiplicity of body parts (e.g., arms, legs, torso). In some embodiments, the ear-worn device can be in electronic communication with the sensors or processor of a medical device (implantable, wearable, external, etc.).

Susceptibility Factors

Various embodiments herein include evaluation of susceptibility factors and the use thereof in various operations. For example, the ear-worn device can be configured to receive an input regarding a susceptibility factor of the ear-worn device wearer. This can be used to change threshold values used by the system. For example, indications of susceptibility can be used to reduce threshold values used by the system (e.g., the system can become more conservative with exposure thresholds if the device wearer has some susceptibility factors present).

Information on susceptibility factors can be obtained in various ways. In some cases, the ear-worn device and/or another component of a system herein can be configured to receive information from an electronic medical record of the device wearer or another type of health-information containing database. The electronic medical record or database entries can include information on various susceptibility factors including, but not limited to, those described herein. In some cases, the ear-worn device and/or another component of a system herein can be configured to query the device wearer in order to get information on various susceptibility factors discussed herein. In some cases, the ear-worn device and/or another component of a system herein can be configured to query a third party (such as a care provider, guardian, clinician, etc.) in order to get information on various susceptibility factors discussed herein.

Further details about exemplary susceptibility factors are provided as follows. However, it will be appreciated that this is merely provided by way of example and that further variations are contemplated herein.

In various embodiments, the susceptibility factor can include at least one of an enlarged vestibular aqueduct (EVA), noise-induced hearing loss, family medical history, genetic testing results, ototoxic medication use, congenital ear deformities, albinism, and exposure to cigarette smoke.

In various embodiments, the susceptibility factor can include at least one medical condition selected from the group consisting of diabetes, heart disease, cancer, and tinnitus.

Protective Countermeasures and Preventative Instructions

Various embodiments herein can include suggesting and/or initiating protective countermeasures. Further details about exemplary protective countermeasures are provided as follows. However, it will be appreciated that this is merely provided by way of example and that further variations are contemplated herein.

Further, various embodiments herein can include suggesting and/or initiating preventative instructions and/or actions. Further details about exemplary preventative instructions and/or actions are provided as follows. However, it will be appreciated that this is merely provided by way of example and that further variations are contemplated herein.

In various embodiments, the ear-worn device 110 is configured to issue preventative instructions to the ear-worn device wearer 118 or a third party 504 if the tracked exposure crosses an instantaneous threshold value or a defined time total of exposure threshold value. In various embodiments, the preventative instructions are provided as at least one of an audible warning, a visual warning, and a haptic warning.

In various embodiments, the ear-worn device 110 is further configured to recognize an activity of the ear-worn device wearer 118 and issue preventative instructions to the ear-worn device wearer 118 or a third party 504 if the recognized activity is one presenting risk crossing a threshold value.

In various embodiments, the ear-worn device 110 is further configured to initiate a protective countermeasure if the tracked exposure crosses an instantaneous threshold value or a defined time total of exposure threshold value.

In various embodiments, the protective countermeasure can include at least one of adjusting at least one of a sound output volume and a frequency filtering setting of the ear-worn device, opening or closing an acoustic vent regulation apparatus, issuing a command to a sound-emitting device to reduce or modify its output of sound or vibration, initiating administration of an active agent to the ear-worn device 110 wearer, initiating a noise-cancellation feature, and guiding or directing the ear-worn device wearer 118 to a different physical location. In various embodiments, guiding or directing the ear-worn device wearer 118 to a different physical location includes guiding or directing the ear-worn device wearer 118 to a physical location that is less noisy than the current physical location. In various embodiments, wherein guiding the ear-worn device wearer 118 to a different physical location includes providing a virtual audio guidance beacon.

As referenced above, one type of protective countermeasure can include opening or closing of an acoustic vent regulation apparatus. By way of example, a vent of the ear-worn device can be closed to block out harmful sound external to the hearing device or can be opened to allow release of potentially harmful sound produced by the hearing device (particularly for the frequency ranges below 1.25 kHz). Aspects related to exemplary acoustic vents and opening and closing of the same are provided in U.S. Pat. No. 8,923,543 and U.S. Appl. No. 62/850,805, the content of both of which are herein incorporated by reference.

In various embodiments, the protective countermeasure can include administration of and/or a suggestion to take or administer an active agent (orally, by injection, etc.). In various embodiments, the active agent can include an antioxidant. In various embodiments, the active agent can include at least one of N-acetylcysteine (NAC), acetyl-L-carnitine, magnesium ($Mg^{2+}$), glutathione selenium, seglutathione peroxidase, beta-carotene (BC), vitamin A, vitamin E, trolox, tocotrienols, tocopherols, stereoisomers, alphalipoic acid, coenzyme Q10, cysteine, a decongestant, saturated hydrogen saline, and fludrocortisone. It will be appreciated that active agents may be administered at any suitable point in time, including at one or more times prior to, during, and after exposure to hearing degrading condition. It will also be appreciated that dosages of active agents may depend on factors relative to the user, including one or more of age, height, weight, sex, presence of a qualifying susceptibility factor, and metrics relative to the user's exposure to hearing degrading condition(s), previous active agent administration(s), and inputs from one or more sensors of the ear-worn device 110 and accessory device 112.

In at least one embodiment, a barometer sensor may be used to determine the relative altitude of the user. It will be appreciated that some antioxidants, such as vitamin E, are more effective as quenchers of free radicals in reduced oxygen pressure, whereas others, such as betacarotene, and vitamin A, are more effective in higher atmospheric pressures; thus information regarding altitude may be used to optimize the effectiveness of an administration of an active agent.

It will be further appreciated that the system may vary administration of active agents to avoid the risks of excessive amounts of each form. For example, it is believed that oxidized forms of vitamin C and vitamin E can also act as radicals; therefore, excessive amounts of any one of these forms, when used as a single agent, could be harmful over a long period of time. Vitamin C also plays an important role in maintaining cellular levels of vitamin E by recycling vitamin E radical (oxidized) to the reduced (antioxidant) form. Also, oxidative DNA damage produced by levels of vitamin C could be protected by vitamin E.

Prediction of Timing for Crossing Thresholds

It can be of immense value to the device wearer to be able to receive a prediction of when they are likely to cross a threshold value of exposure to hearing degrading conditions. By way of example, if a device wearer is exposed to hearing degrading conditions at work and the ear-worn device (or another system component) informs them that they only have 2 hours left until a threshold will be reached, but 4 hours left on their shift, then they can tell this to a manager and, possibly, complete a portion of the remainder of their shift in a quieter area. In some embodiments, the system can automatically notify an employer that the user is nearing a hearing dose limit, on behalf of the user. Similarly, if the device wearer learns that they are likely to reach a threshold level of exposure in a relatively short period of time, then they can start to prepare to leave their current location to find a quieter area (such as a device wearer at a rock concert).

In various embodiments herein, the ear-worn device 110 is configured to predict when an ear-worn device wearer 118 will cross a threshold value based on prior exposure data. In some embodiments, the prediction can be performed as simply as a straight-line extrapolation based on data over a previous time period (which can be an immediately previous time period or a representative time period). For example, if the device wearer has been exposed to an amount equal to "X" over the last hour, then the ear-worn device or another system device can calculate how much longer it will take to reach a threshold value at that same rate (e.g., the accuracy of this method of prediction depends on the exposure rate staying relatively static).

However, in other embodiments, more sophisticated techniques can be used to improve predictive accuracy. By way of example, in one approach, units of a day can be divided up into characteristic periods. In the example of a work day, the day can be divided up into periods of nighttime sleeping, wakeful morning time at home, time at work, and then wakeful evening time at home. The onset of each period can be determined as a matter of input from the user and/or from observing sensor data (including but not limited to accelerometer data) over time. Then, statistics regarding exposure rates can be determined for each characteristic period. A prediction of when a threshold of exposure will be reached is then based on differing statistics regarding exposure rates during these different periods of time.

In yet another example of prediction, machine learning approaches can be used on data that is gathered from the device wearer over a period of time. The output of such analysis can include statistics regarding exposure rate as a function of various factors such as the time of the day, the day of the week, the sensed activity level, or any other piece of data that can be fed into the machine learning algorithm including sensor data of any of the sensors discussed herein. The output of such analysis can also include the timing of typical transition points in exposure (e.g., a given individual typically experiences a substantial drop off in exposure at 5 PM). Then, using this data, a predicted time for crossing a threshold value can be determined. For example, if it is current 3 PM, but a typical transition in exposure occurs at 4 PM, then an average rate of exposure for the time period of 3 PM to 4 PM can be assumed followed by a second average rate of exposure that is applicable for 4 PM until a later time.

In some embodiments, calendared or otherwise scheduled events can be used in order to improve predictions herein. By way of example, if a device wearer is scheduled to attend an event, then information regarding the event can be used to provide better predictions about exposure the device wearer will receive and when thresholds of exposure may be crossed. For example, if the device wearer is scheduled to attend a sporting event, then information regarding average noise volumes at the sporting event and the expected length of time of the sporting event can be used to aid in determining predicted exposure and when a threshold may be crossed. Similarly, if the device wearer is scheduled to attend a concert, then information regarding average noise volumes at the concert and the expected duration of the concert can be used to aid in determining predicted exposure and when a threshold may be crossed.

Calculations relative to exposure statistics may be based upon individual device user data and trends or based upon data and trends aggregated from a group of individuals, such as coworkers or individuals who are currently at (or have previously visited) a location approximate to the device user. In some exemplary embodiments, the machine learning techniques employed by the system may be used to classify a current acoustical environment with one or more previous acoustical environment of the device user or a group of individuals. In at least one embodiment, prior data may be collected from an individual device user or larger group of individuals at locations geographically distinct from where the device user is presently. Many other predictive techniques are explicitly contemplated herein.

Further Embodiments

In an embodiment, an ear-worn device is included having a control circuit, a microphone in electrical communication with the control circuit, an electroacoustic transducer for generating sound in electrical communication with the control circuit, and a power supply circuit in electrical communication with the control circuit, wherein the ear-worn device is configured to track exposure to hearing degrading conditions over time via at least one of the microphone and a sensor package and wherein the ear-worn device is configured to store data regarding the tracked exposure.

In an embodiment, in addition to one or more of the preceding or following embodiments, or in the alternative to some embodiments, the sensor package can include at least one of a motion sensor, an oximeter, a glucometer, an air pressure sensor, a heart rate sensor, a blood pressure sensor, and an ambient air chemical sensor.

In an embodiment, in addition to one or more of the preceding or following embodiments, or in the alternative to some embodiments, the stored data regarding tracked exposure can include sound volume or vibration exposure, duration of exposure, and at least one of concurrent movement, concurrent position, concurrent oxygen saturation, concurrent blood glucose concentrations, concurrent heart rate, concurrent blood pressure, and concurrent ambient air chemical sensor data.

In an embodiment, in addition to one or more of the preceding or following embodiments, or in the alternative to some embodiments, stored data regarding tracked exposure can include sound volume or vibration exposure, duration of exposure, and a risk index factor calculated using at least one of concurrent movement, concurrent position, concurrent oxygen saturation, concurrent blood glucose concentrations, concurrent heart rate, concurrent blood pressure, concurrent ambient air chemical sensor data, and sound or vibration exposure during a preceding time period.

In an embodiment, in addition to one or more of the preceding or following embodiments, or in the alternative to some embodiments, the ear-worn device or an accessory device in communication therewith can further be configured to issue a warning if the tracked exposure crosses a dynamic threshold based upon a time period's combined exposure intensity and duration.

In an embodiment, in addition to one or more of the preceding or following embodiments, or in the alternative to some embodiments, the ear-worn device or an accessory device in communication therewith can be further configured to issue a warning if the tracked exposure crosses an instantaneous threshold value or a defined time total of exposure threshold value.

In an embodiment, in addition to one or more of the preceding or following embodiments, or in the alternative to some embodiments, the warning can be provided as at least one of an audible warning, a visual warning, and a haptic warning.

In an embodiment, in addition to one or more of the preceding or following embodiments, or in the alternative to some embodiments, the warning can be provided to at least one of the ear-worn device wearer and a third party.

In an embodiment, in addition to one or more of the preceding or following embodiments, or in the alternative to some embodiments, the ear-worn device or an accessory device in communication therewith can be further configured to issue preventative instructions to the ear-worn device wearer if the tracked exposure crosses an instantaneous threshold value or a defined time total exposure threshold value.

In an embodiment, in addition to one or more of the preceding or following embodiments, or in the alternative to some embodiments, the preventative instructions can be provided as at least one of an audible warning, a visual warning, and a haptic warning.

In an embodiment, in addition to one or more of the preceding or following embodiments, or in the alternative to some embodiments, the ear-worn device or an accessory device in communication therewith can be configured to predict when an ear-worn device wearer will cross a threshold value.

In an embodiment, in addition to one or more of the preceding or following embodiments, or in the alternative to some embodiments, the ear-worn device or an accessory device in communication therewith can be configured to predict when an ear-worn device wearer will cross a threshold value based on prior exposure data.

In an embodiment, in addition to one or more of the preceding or following embodiments, or in the alternative to some embodiments, the ear-worn device or an accessory device in communication therewith can be configured to send a prediction of when an ear-worn device wearer will cross a threshold value to an employer.

In an embodiment, in addition to one or more of the preceding or following embodiments, or in the alternative to some embodiments, the ear-worn device or an accessory device in communication therewith can be further configured to initiate a protective countermeasure if the tracked exposure crosses an instantaneous threshold value or a defined time total of exposure threshold value.

In an embodiment, in addition to one or more of the preceding or following embodiments, or in the alternative to some embodiments, the ear-worn device or an accessory device in communication therewith can be further configured to initiate a protective countermeasure if exposure is anticipated to cross an instantaneous threshold value or a defined time total of exposure threshold value.

In an embodiment, in addition to one or more of the preceding or following embodiments, or in the alternative to some embodiments, the protective countermeasure can include at least one of adjusting at least one of a sound output volume and a frequency filtering setting of the ear-worn device, issuing a command to a sound-emitting device to reduce sound volume, opening or closing an acoustic vent regulation apparatus, initiating administration of an active agent to the ear-worn device wearer, initiating a noise-cancellation feature, and guiding or directing the ear-worn device wearer to a different physical location.

In an embodiment, in addition to one or more of the preceding or following embodiments, or in the alternative to some embodiments, guiding or directing the ear-worn device wearer to a different physical location includes guiding or directing the ear-worn device wearer to a physical location that is less noisy than the current physical location.

In an embodiment, in addition to one or more of the preceding or following embodiments, or in the alternative to some embodiments, guiding or directing the ear-worn device wearer to a different physical location includes providing a virtual audio guidance beacon.

In an embodiment, in addition to one or more of the preceding or following embodiments, or in the alternative to some embodiments, the active agent can include an antioxidant.

In an embodiment, in addition to one or more of the preceding or following embodiments, or in the alternative to some embodiments, the active agent can include at least one of N-acetylcysteine (NAC), acetyl-L-carnitine, magnesium (Mg2+), glutathione selenium, seglutathione peroxidase, beta-carotene (BC), vitamin A, vitamin E, trolox, tocotrienols, tocopherols, stereoisomers, alpha-lipoic acid, coenzyme Q10, cysteine, a decongestant, saturated hydrogen saline, and fludrocortisone.

In an embodiment, in addition to one or more of the preceding or following embodiments, or in the alternative to some embodiments, the ear-worn device or an accessory device in communication therewith can be further configured to receive an input regarding a susceptibility factor of the ear-worn device wearer.

In an embodiment, in addition to one or more of the preceding or following embodiments, or in the alternative to some embodiments, the susceptibility factor can include at least one of a medical condition, enlarged vestibular aqueduct (EVA), noise-induced hearing loss, family medical history, genetic testing results, ototoxic medication use, and exposure to cigarette smoke.

In an embodiment, in addition to one or more of the preceding or following embodiments, or in the alternative to some embodiments, the medical condition selected from the group consisting of enlarged vestibular aqueduct (EVA), diabetes, heart disease, cancer, congenital ear deformities, albinism, and tinnitus.

In an embodiment, in addition to one or more of the preceding or following embodiments, or in the alternative to some embodiments, the tracked exposure to hearing degrading conditions can include head movement crossing a threshold value.

In an embodiment, in addition to one or more of the preceding or following embodiments, or in the alternative to some embodiments, the tracked exposure to hearing degrading conditions can include air pressure changes crossing a threshold value.

In an embodiment, in addition to one or more of the preceding or following embodiments, or in the alternative to some embodiments, the ear-worn device or an accessory device in communication therewith can be configured to adjust settings of the ear-worn device based on the tracked exposure to hearing degrading conditions.

In an embodiment, in addition to one or more of the preceding or following embodiments, or in the alternative to some embodiments, the ear-worn device or an accessory device in communication therewith can be configured to adjust settings of the ear-worn device based on anticipated exposure to hearing degrading conditions.

In an embodiment, in addition to one or more of the preceding or following embodiments, or in the alternative to some embodiments, the stored data regarding tracked exposure further includes contributions to exposure provided by the ear-worn device itself.

In an embodiment, in addition to one or more of the preceding or following embodiments, or in the alternative to some embodiments, the ear-worn device or an accessory device in communication therewith can be configured to output stored data regarding tracked exposure to an electronic medical record or other health-information related database.

In an embodiment, in addition to one or more of the preceding or following embodiments, or in the alternative to some embodiments, the ear-worn device or an accessory device in communication therewith can be configured to store data regarding tracked exposure longitudinally.

In an embodiment, in addition to one or more of the preceding or following embodiments, or in the alternative to some embodiments, the ear-worn device or an accessory device in communication therewith can be further configured to determine a direction of a predominant source of noise in an environment and direct the device wearer to orient themselves in order to reduce and/or attenuate exposure.

In an embodiment, in addition to one or more of the preceding or following embodiments, or in the alternative to some embodiments, the ear-worn device or an accessory device in communication therewith can be further configured to determine a direction of a predominant source of noise in an environment and direct the device wearer to orient themselves such that the predominant noise source is located in the direction of the ear-worn device's directional microphone null.

In an embodiment, an ear-worn device is included having a control circuit, a microphone in electrical communication with the control circuit, an electroacoustic transducer for generating sound in electrical communication with the control circuit, and a power supply circuit in electrical communication with the control circuit, wherein the ear-worn device is configured to track exposure to conditions which can degrade hearing in an ear-worn device wearer having an enlarged vestibular aqueduct (EVA) over time via at least one of the microphone and a sensor package. In various embodiments the ear-worn device is configured to store data regarding the tracked exposure. In various embodiments the sensor package includes at least one of a motion sensor and a pressure sensor.

In an embodiment, in addition to one or more of the preceding or following embodiments, or in the alternative to some embodiments, the tracked exposure to conditions which can degrade hearing in an ear-worn device wearer having an enlarged vestibular aqueduct (EVA) over time can include head movement crossing a threshold value.

In an embodiment, in addition to one or more of the preceding or following embodiments, or in the alternative to some embodiments, the tracked exposure to conditions which can degrade hearing in an ear-worn device wearer having an enlarged vestibular aqueduct (EVA) over time can include a detected head impact.

In an embodiment, in addition to one or more of the preceding or following embodiments, or in the alternative to some embodiments, the tracked exposure to conditions which can degrade hearing in an ear-worn device wearer having an enlarged vestibular aqueduct (EVA) over time can include air pressure changes crossing a threshold value.

In an embodiment, in addition to one or more of the preceding or following embodiments, or in the alternative to some embodiments, the ear-worn device or an accessory device in communication therewith can be further configured to issue a warning if the tracked exposure crosses an instantaneous threshold value or a defined time total exposure threshold value.

In an embodiment, in addition to one or more of the preceding or following embodiments, or in the alternative to some embodiments, the warning can be provided as at least one of an audible warning, a visual warning, and a haptic warning.

In an embodiment, in addition to one or more of the preceding or following embodiments, or in the alternative to some embodiments, the warning can be provided to at least one of the ear-worn device wearer and a third party.

In an embodiment, in addition to one or more of the preceding or following embodiments, or in the alternative to some embodiments, the ear-worn device or an accessory device in communication therewith can be further configured to issue preventative instructions to the ear-worn device wearer or a third party if the tracked exposure crosses an instantaneous threshold value or a defined time total of exposure threshold value.

In an embodiment, in addition to one or more of the preceding or following embodiments, or in the alternative to some embodiments, the ear-worn device or an accessory device in communication therewith can be further configured to issue preventative instructions to the ear-worn device wearer or a third party if anticipated exposure crosses an instantaneous threshold value or a defined time total of exposure threshold value.

In an embodiment, in addition to one or more of the preceding or following embodiments, or in the alternative to some embodiments, the ear-worn device or an accessory device in communication therewith can be further configured to recognize an activity of the ear-worn device wearer and issue preventative instructions to the ear-worn device wearer or a third party if the recognized activity is one presenting risk crossing a threshold value.

In an embodiment, in addition to one or more of the preceding or following embodiments, or in the alternative to some embodiments, the preventative instructions can be provided as at least one of an audible warning, a visual warning, and a haptic warning.

In an embodiment, in addition to one or more of the preceding or following embodiments, or in the alternative to some embodiments, the ear-worn device or an accessory device in communication therewith can be further configured to initiate a protective countermeasure if the tracked exposure crosses an instantaneous threshold value or a defined time total of exposure threshold value.

In an embodiment, a method of monitoring hearing loss progression is included, the method including tracking exposure to hearing degrading conditions over time with an ear-worn device, storing data regarding the tracked exposure, and performing at least one of issuing a warning when the tracked exposure crosses an instantaneous threshold value or a defined time total of exposure threshold value, issuing preventative instructions to the ear-worn device wearer when the tracked exposure crosses an instantaneous threshold value or a defined time total exposure threshold value, and initiating a protective countermeasure when the tracked exposure crosses an instantaneous threshold value or a defined time total of exposure threshold value.

In an embodiment, in addition to one or more of the preceding or following embodiments, or in the alternative to some embodiments, the ear-worn device of the method can include a control circuit, a microphone in electrical communication with the control circuit, an electroacoustic transducer for generating sound in electrical communication with the control circuit, a power supply circuit in electrical communication with the control circuit, and a sensor package can include at least one of a motion sensor, an oximeter, a glucometer, an air pressure sensor, a heart rate sensor, a blood pressure sensor, and an ambient air chemical sensor.

In an embodiment, in addition to one or more of the preceding or following embodiments, or in the alternative to some embodiments, the method can further include issuing a warning when the tracked exposure crosses a dynamic threshold based upon a time period's combined exposure intensity and duration.

In an embodiment, in addition to one or more of the preceding or following embodiments, or in the alternative to some embodiments, the method can further include issuing a warning when the tracked exposure crosses an instantaneous threshold value or a defined time total of exposure threshold value.

In an embodiment, in addition to one or more of the preceding or following embodiments, or in the alternative to some embodiments, the method can further include issuing preventative instructions to the ear-worn device wearer of a third party when the tracked exposure crosses an instantaneous threshold value or a defined time total exposure threshold value.

In an embodiment, in addition to one or more of the preceding or following embodiments, or in the alternative to some embodiments, can further include predicting when an ear-worn device wearer will cross a threshold value.

In an embodiment, in addition to one or more of the preceding or following embodiments, or in the alternative to some embodiments, can further include predicting when an ear-worn device wearer will cross a threshold value based on prior exposure data.

In an embodiment, in addition to one or more of the preceding or following embodiments, or in the alternative to some embodiments, can further include sending a prediction of when an ear-worn device wearer will cross a threshold value to an employer.

In an embodiment, in addition to one or more of the preceding or following embodiments, or in the alternative to some embodiments, can further include issuing preventative instructions to the ear-worn device wearer or a third party when exposure is anticipated to cross an instantaneous threshold value or a defined time total of exposure threshold value.

In an embodiment, in addition to one or more of the preceding or following embodiments, or in the alternative to some embodiments, can further include initiating a protective countermeasure when the tracked exposure crosses an instantaneous threshold value or a defined time total of exposure threshold value.

In an embodiment, in addition to one or more of the preceding or following embodiments, or in the alternative to some embodiments, can further include guiding or directing the ear-worn device wearer to a physical location that is less noisy than the current physical location.

In an embodiment, in addition to one or more of the preceding or following embodiments, or in the alternative to some embodiments, can further include adjusting settings of the ear-worn device based on the tracked exposure to hearing degrading conditions.

In an embodiment, in addition to one or more of the preceding or following embodiments, or in the alternative to some embodiments, can further include adjusting settings of the ear-worn device based on anticipated exposure to hearing degrading conditions.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An ear-worn device comprising:
a control circuit;
a microphone in electrical communication with the control circuit;
an electroacoustic transducer for generating sound in electrical communication with the control circuit;
a power supply circuit in electrical communication with the control circuit;
wherein the ear-worn device is configured to track exposure to hearing degrading conditions over time via at least one of the microphone and a sensor package;
wherein the ear-worn device is configured to store data regarding the tracked exposure;
wherein the ear-worn device or an accessory device in communication therewith is further configured to issue a warning if the tracked exposure crosses a dynamic threshold; and
wherein the ear-worn device or the accessory device is further configured to receive an input regarding a susceptibility factor of the ear-worn device wearer, the susceptibility factor comprising at least one of enlarged vestibular aqueduct (EVA);
diabetes;
heart disease;
cancer;
congenital ear deformities;
albinism;
tinnitus;
noise-induced hearing loss;
genetic testing results;
ototoxic medication use; and
exposure to cigarette smoke;
wherein the dynamic threshold is adjusted based on the ear-worn device wearer having one or more of the susceptibility factors.

2. The ear-worn device of claim 1, the stored data regarding tracked exposure comprising
sound volume or vibration exposure;
duration of exposure; and
at least one of
concurrent movement;
concurrent position;
concurrent oxygen saturation;
concurrent blood glucose concentrations;
concurrent heart rate;
concurrent blood pressure; and
concurrent ambient air chemical sensor data.

3. The ear-worn device of claim 1, wherein stored data regarding tracked exposure comprising sound volume or vibration exposure;
duration of exposure; and
a risk index factor calculated using at least one of
concurrent movement;
concurrent position;
concurrent oxygen saturation;
concurrent blood glucose concentrations;
concurrent heart rate;
concurrent blood pressure;
concurrent ambient air chemical sensor data; and sound or vibration exposure during a preceding time period.

4. The ear-worn device of claim 1, the dynamic threshold is based upon a time period's combined exposure intensity and duration.

5. The ear-worn device of claim 1, wherein the ear-worn device or an accessory device in communication therewith is further configured to issue a warning if the tracked exposure crosses an instantaneous threshold value or a defined time total of exposure threshold value.

6. The ear-worn device of claim 1, wherein the ear-worn device or an accessory device in communication therewith is further configured to issue preventative instructions to the ear-worn device wearer if the tracked exposure crosses an instantaneous threshold value or a defined time total exposure threshold value.

7. The ear-worn device of claim 1, wherein the ear-worn device or an accessory device in communication therewith is configured to predict when an ear-worn device wearer will cross a threshold value of tracked exposure based on prior exposure data.

8. The ear-worn device of claim 1, wherein the ear-worn device or an accessory device in communication therewith is further configured to initiate a protective countermeasure if the tracked exposure crosses an instantaneous threshold value or a defined time total of exposure threshold value.

9. The ear-worn device of claim 8, the protective countermeasure comprising at least one of adjusting at least one of a sound output volume and a frequency filtering setting of the ear- worn device;

issuing a command to a sound-emitting device to reduce sound volume;

opening or closing an acoustic vent regulation apparatus;

initiating administration of an active agent to the ear-worn device wearer;

initiating a noise-cancellation feature; and guiding or directing the ear-worn device wearer to a different physical location.

10. The ear-worn device of claim 1, the tracked exposure to hearing degrading conditions comprising air pressure changes crossing a threshold value.

11. The ear-worn device of claim 1, wherein the ear-worn device or an accessory device in communication therewith is further configured to determine a direction of a predominant source of noise in an environment and direct the device wearer to orient themselves in order to reduce and/or attenuate exposure.

12. The ear-worn device of claim 1, wherein the ear-worn device or an accessory device in communication therewith is further configured to determine a direction of a predominant source of noise in an environment and direct the device wearer to orient themselves such that the predominant noise source is located in the direction of the ear-worn device's directional microphone null.

13. A method of monitoring hearing loss progression comprising:

tracking exposure to hearing degrading conditions over time with an ear-worn device;

storing data regarding the tracked exposure; and performing at least one of issuing a warning when the tracked exposure crosses an instantaneous threshold value or a defined time total of exposure threshold value;

issuing preventative instructions to the ear-worn device wearer when the tracked exposure crosses an instantaneous threshold value or a defined time total exposure threshold value; and initiating a protective countermeasure when the tracked exposure crosses an instantaneous threshold value or a defined time total of exposure threshold value; and determining a direction of a predominant source of noise in an environment and directing the device wearer to orient themselves such that the predominant noise source is located in the direction of a directional microphone null of the ear-worn device.

14. The method of claim 13, further comprising initiating a protective countermeasure when the tracked exposure crosses an instantaneous threshold value or a defined time total of exposure threshold value.

15. The method of claim 13, further comprising guiding or directing the ear-worn device wearer to a physical location that is less noisy than the current physical location.

16. The method of claim 13, further comprising adjusting settings of the ear-worn device based on the tracked exposure to hearing degrading conditions.

17. An ear-worn device comprising:

a control circuit;

a microphone in electrical communication with the control circuit;

an electroacoustic transducer for generating sound in electrical communication with the control circuit;

a power supply circuit in electrical communication with the control circuit;

wherein the ear-worn device is configured to track exposure to hearing degrading conditions over time via at least one of the microphone and a sensor package;

wherein the ear-worn device is configured to store data regarding the tracked exposure; and wherein the ear-worn device or an accessory device in communication therewith is further configured to determine a direction of a predominant source of noise in an environment and direct the device wearer to orient themselves in order to reduce and/or attenuate exposure.

18. The ear-worn device of claim 9, wherein the protective countermeasure comprises closing a vent of the ear-worn device to block external sound.

19. The ear-worn device of claim 1, wherein the dynamic threshold is decreased based on the ear-worn device wearer having one or more of the susceptibility factors.

* * * * *